US011207523B2

(12) United States Patent
Ternes et al.

(10) Patent No.: US 11,207,523 B2
(45) Date of Patent: Dec. 28, 2021

(54) HIS-BUNDLE PACING FOR RATE REGULARIZATION

(71) Applicant: Cardiac Pacemakers, Inc., St. Paul, MN (US)

(72) Inventors: David J. Ternes, Roseville, MN (US); Deepa Mahajan, North Oaks, MN (US); Keith L. Herrmann, Minneapolis, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 185 days.

(21) Appl. No.: 16/691,171

(22) Filed: Nov. 21, 2019

(65) Prior Publication Data

US 2020/0179692 A1 Jun. 11, 2020

Related U.S. Application Data

(60) Provisional application No. 62/777,554, filed on Dec. 10, 2018.

(51) Int. Cl.
*A61N 1/362* (2006.01)
*A61N 1/365* (2006.01)

(52) U.S. Cl.
CPC ....... *A61N 1/3624* (2013.01); *A61N 1/36592* (2013.01)

(58) Field of Classification Search
None
See application file for complete search history.

(56) References Cited

U.S. PATENT DOCUMENTS

| | | | |
|---|---|---|---|
| 6,718,206 B2 | 4/2004 | Casavant | |
| 8,588,907 B2 | 11/2013 | Arcot-Krishnamurthy et al. | |
| 9,079,034 B2 | 7/2015 | Milbocker | |
| 2002/0120318 A1 | 8/2002 | Kroll et al. | |
| 2003/0078625 A1* | 4/2003 | Casavant | A61N 1/3627 607/9 |

OTHER PUBLICATIONS

Huang, Weijian, et al., "Benefits of Permanent His Bundle Pacing Combined With Atrioventricular Node Ablation in Atrial Fibrillation Patients With Heart Failure With Both Preserved and Reduced Left Ventricular Ejection Fraction", J Am Heart Assoc. 2017;6:e005309; originally published Apr. 1, 2017, 1-11.
Padeletti, Luigi, et al., "Rate stabilization by right ventricular apex or His bundle pacing in patients with atrial fibrillation", The European Society of Cardiology. Europace (2005) 7, 454-459.

* cited by examiner

*Primary Examiner* — Paula J Stice
(74) *Attorney, Agent, or Firm* — Schwegman Lundberg & Woessner P.A.

(57) ABSTRACT

Systems and methods for pacing cardiac conductive tissue are described. An exemplary system includes an electrostimulation circuit that may generate HBP pulses to stimulate patient physiologic conduction pathway, such as a His bundle or a bundle branch. The system includes an arrhythmia detector to detect an atrial tachyarrhythmia (AT) with intermittent ventricular conduction. A control circuit may sense ventricular activation and, in response to the detected AT indication, determine or update a His-bundle pacing (HBP) configuration. The HBP may be recursively updated on a beat-by-beat basis using the sensed ventricular activation. The electrostimulation circuit may deliver HBP according to the determined or adjusted HBP configuration to regularize ventricular rate during AT.

20 Claims, 7 Drawing Sheets

HIS-BUNDLE PACING FOR RATE REGULARIZATION

CLAIM OF PRIORITY

This application claims the benefit of priority under 35 U.S.C. § 119(e) of U.S. Provisional Patent Application Ser. No. 62/777,554, filed on Dec. 10, 2018, which is herein incorporated by reference in its entirety.

TECHNICAL FIELD

This document relates generally to medical systems, and more particularly, to systems, devices and methods for pacing of cardiac conductive tissue, such as a His bundle or a bundle branch.

BACKGROUND

The heart is the center of a person's circulatory system. It includes an electro-mechanical system performing two major pumping functions. The left portions of the heart, including the left atrium (LA) and left ventricle (LV), draw oxygenated blood from the lungs and pump it to the organs of the body to provide the organs with their metabolic needs for oxygen. The right portions of the heart, including the right atrium (RA) and right ventricle (RV), draw deoxygenated blood from the body organs and pump it to the lungs where the blood gets oxygenated. These pumping functions result from contractions of the myocardium (cardiac muscles). In a normal heart, the sinoatrial (SA) node, the heart's natural pacemaker, generates electrical pulses, called action potentials, which propagate through natural electrical conduction pathways known as His-Purkinje system to various regions of the heart to excite the myocardial tissue of the heart. For example, the action potentials originated from the SA node propagate through the atrioventricular (AV) node, the His bundle (also known as Bundle of His), the bundle branches, and Purkinje fibers to reach the ventricular myocardium, resulting in coordinated contractions in both ventricles.

Coordinated delays in the propagation of the action potentials in a normal electrical conduction system cause the various portions of the heart to contract in synchrony to result in efficient pumping functions. A blocked or otherwise abnormal electrical conduction and/or deteriorated myocardium may cause asynchronous contraction of the heart, resulting in poor hemodynamic performance, including a diminished blood supply to the heart and the rest of the body. For example, an abnormal delay in the transmission of the action potentials in the His bundle may cause irregular or asynchronous contractions of the ventricles, resulting in an abnormal rhythm of the heart.

Artificial cardiac pacing system have been used to rectify cardiac dyssynchrony and to improve hemodynamic performance. The artificial cardiac pacing system may provide electrical stimulations to one or more portions of the heart such as to restore normal functioning of the heart to a certain extent. For example, right ventricular pacing via electrodes implanted in the apex of the RV have been used in both single ventricular and biventricular (BiV) pacing. RV apex pacing directly excites the ventricular myocardium, rather than propagating the action potentials through the natural conduction pathways. Studies have shown that, in some patients, long-term RV apex pacing may result in loss of synchronous mechanical contraction of RV and LV, partially due to the interventricular delay in impulse propagation to the left ventricle. Consequently, permanent changes in myocardial perfusion and structure may develop over time in these patients, which may further decrease cardiac output and deteriorate ventricular function. BiV pacing involves RV pacing via one lead, and LV pacing via another lead, and has been demonstrated to restore synchronized contraction of both ventricles. However, the potential adverse impact on ventricular function produced by the RV apex pacing may still exist in BiV pacing. Additionally, compared to cardiac depolarization through AV node activation and propagation through the natural conduction pathways, the BiV pacing may not produce similarly coordinated cardiac contractions. Moreover, the surgical procedure for placing the LV lead through the coronary sinus and into a vein on the left ventricular wall may be complex and challenging in some patients.

Atrial fibrillation (AF) is the most common cardiac arrhythmia and confers substantial mortality and morbidity from stroke, thrombo-embolism, heart failure, and impaired quality of life. Some patients with cardiac diseases such as chronic heart failure (HF) may experience episodes of atrial tachyarrhthmia (AT), such as atrial fibrillation (AF). Although AF episodes may not be immediately life threatening, they may be associated with various symptoms, a reduced quality of life, and a reduced cardiac output. For example, during AF episodes, the ventricular rate may become irregular if such patients have intact atrioventricular (AV) conduction. Irregular ventricular rates due to AT may cause patient discomfort, decrease cardiac output, increase susceptibility to ventricular tachyarrhythmia, deteriorate cardiac hemodynamic function, and exacerbate heart failure status Symptomatic AF patients are typically treated with drugs to suppress AF episodes and restore sinus rhythm, known as "rhythm control" of AF. However, the "rhythm control" therapies may not be effective, and may have undesirable side effects. An alternative therapy involves drugs to reduce and stabilize the ventricular heart rate, known as ventricular "rate control". However, it may be difficult to achieve rate control during AF using pharmacological agents alone in some patients, due to ineffective drugs, side effects, contraindications, or lack of patient compliance. When patients fail rhythm control or rate control therapies, they may be treated with AV nodal ablation and pacemaker implantation. AV node ablation is undesirable because it causes irreversible destruction of the AV node, results in the patient being pacemaker dependent, and is associated with an increased risk for sudden cardiac death.

OVERVIEW

This document discusses systems, devices, and methods for stimulating a patient physiologic conduction pathway to regularize ventricular rate during atrial tachyarrhythmia (AT). An exemplary medical system includes an electrostimulation circuit that may generate His-bundle pacing (HBP) pulses to stimulate the physiologic conduction pathway, such as a His bundle or a bundle branch of the heart. The system includes an arrhythmia detector to detect an AT episode with intermittent ventricular conduction. A control circuit may sense ventricular activation and, in response to the detected AT indication, determine an HBP configuration, such as an HBP pacing rate or timing of HBP. The control circuit may update the HBP configuration on a beat-by-beat basis for each ventricular beat. The electrostimulation circuit may stimulate the physiologic conduction pathway according to the HBP configuration to regularize His bundle activation rate and thus the ventricular rate during AT.

Example 1 is a medical-device system for pacing a physiologic conduction pathway including a His bundle or a bundle branch of the heart. The system comprises an arrhythmia detector configured to detect an atrial tachyarrhythmia (AT) indication with intermittent ventricular conduction, and a control circuit. The control circuit can be configured to receive information of ventricular activation; in response to a detected AT indication, determine a His-bundle pacing (HBP) configuration using the received information of ventricular activation; and control an electrostimulation circuit configured to generate HBP pulses, and provide a control signal to deliver the generated HBP pulses to stimulate a physiologic conduction pathway of a heart of the patient in accordance with the determined HBP configuration to regularize ventricular activation rate.

In Example 2, the subject matter of Example 1 optionally includes the control circuit that can be configured to determine the HBP configuration including an HBP pacing rate, an HBP pacing interval, or HBP pacing timing.

In Example 3, the subject matter of any one or more of Examples 1-2 optionally includes the electrostimulation circuit, and the control circuit that can be configured to detect ventricular beats from the received information of ventricular activation, and in response to the detected AT indication, update the HBP configuration on a beat-by-beat basis using the detected ventricular beats. The electrostimulation circuit can be configured to stimulate the physiologic conduction pathway in accordance with the updated HBP configuration.

In Example 4, the subject matter of Example 3 optionally includes the HBP configuration that can include an HBP pacing interval, and the control circuit can be configured to measure a ventricular cycle length (VCL) of the detected ventricular beats, and to update the HBP pacing interval using a weighted combination of a previous HBP pacing interval and the measured VCL each scaled by respective weight factors.

In Example 5, the subject matter of Example 4 optionally includes, in response to an intrinsic ventricular activation sensed prior to expiration of the determined HBP pacing interval, the electrostimulation circuit that can be configured to abort stimulation of the physiologic conduction pathway upon the expiration of the determined HBP pacing interval; and the control circuit that can be configured to reset the HBP pacing interval with reference to the sensed intrinsic ventricular activation.

In Example 6, the subject matter of any one or more of Examples 4-5 optionally includes the control circuit that can be configured to determine the HBP pacing interval to be within a specified range between a lower pacing rate limit and a maximum pacing rate limit.

In Example 7, the subject matter of any one or more of Examples 4-6 optionally includes the control circuit that can be configured to recognize the sensed ventricular activation as either a ventricular response to the HBP pulses (VSH) or an intrinsically conducted ventricular activation (VSI), and determine one or more of the respective weight factors for the previous HBP pacing rate and for the measured VCL using the recognized sensed ventricular activation.

In Example 8, the subject matter of Example 7 optionally includes the control circuit that can be configured to determine a first weight factor for the measured VCL if the sensed ventricular activation is recognized as a VSH, and to determine a second weight factor, smaller than the first weight factor, for the measured VCL if the sensed ventricular activation is recognized as a VSI.

In Example 9, the subject matter of any one or more of Examples 7-8 optionally includes the control circuit that can be configured to increase the HBP pacing interval if the sensed ventricular activation is recognized as a VSH, or to decrease the HBP pacing interval if the sensed ventricular activation is recognized as a VSI.

In Example 10, the subject matter of any one or more of Examples 7-9 optionally includes the control circuit that can be configured to recognize the sensed ventricular activation as either a VSH or a VSI using timing or morphology information of the sensed ventricular activation with reference to a fiducial point.

In Example 11, the subject matter of any one or more of Examples 7-10 optionally includes the control circuit that can be further configured to: determine a ventricular activation pattern including one or more previous ventricular activations followed by the recognized sensed ventricular activation, the one or more previous ventricular activations each including a VSI, a VSH, or a ventricular paced (VP) event; and determine one or more of the respective weight factors for the previous HBP pacing rate and for the measured VCL using the determined ventricular activation pattern.

In Example 12, the subject matter of Example 11 optionally includes the ventricular activation pattern that can include one of: a VSH followed by a VSI; a VSI followed by a VSI; a VP followed by a VSI; a VSH followed by a VSH; a VSI followed by a VSH; or a VP followed by a VSH.

In Example 13, the subject matter of any one or more of Examples 4-12 optionally includes the control circuit that can be configured to detect a fusion between an intrinsically His bundle activation and an HBP pulse using timing information or morphology of the sensed ventricular activation, and recognize the sensed ventricular activation as a VSI in response to the detected fusion.

In Example 14, the subject matter of any one or more of Examples 1-13 optionally includes the arrhythmia detector that can be configured to detect the AT indication using a transition from an atrial tracking-mode to a non-atrial tracking mode.

In Example 15, the subject matter of any one or more of Examples 1-13 optionally includes the arrhythmia detector that can be configured to monitor a frequency of HBP delivery within a specified time period, and to detect the AT indication using a decrease in the frequency of HBP delivery.

Example 16 is a method for pacing a physiologic conduction pathway including a His bundle or a bundle branch of the heart. The method comprises steps of: detecting an atrial tachyarrhythmia (AT) indication with intermittent ventricular conduction; receiving information of ventricular activation; in response to the detected AT indication, determining a His-bundle pacing (HBP) configuration using the received information of ventricular activation; and delivering HBP pulses to stimulate the physiologic conduction pathway in accordance with the determined HBP configuration to regularize ventricular activation rate.

In Example 17, the subject matter of Example 16 optionally includes, determining the HBP configuration that can include detecting ventricular beats from the received information of ventricular activation, and updating the HBP configuration on a beat-by-beat basis using the detected ventricular beats.

In Example 18, the subject matter of Example 17 optionally includes determining the HBP configuration that can include measuring a ventricular cycle length (VCL) corresponding to the detected ventricular beats, and updating an HBP pacing interval using a weighted combination of a previous HBP pacing interval and the measured VCL each scaled by respective weight factors.

In Example 19, the subject matter of Example 18 optionally includes steps of: recognizing the sensed ventricular activation as either a ventricular response to the HBP pulses (VSH) or an intrinsically conducted ventricular activation (VSI); and determining one or more of the respective weight factors for the previous HBP pacing rate and for the measured VCL using the recognized sensed ventricular activation.

In Example 20, the subject matter of Example 19 optionally includes determining the one or more of the respective weight factors that can include determining a first weight factor for the measured VCL if the sensed ventricular activation is recognized as a VSH, and determining a second weight factor, smaller than the first weight factor, for the measured VCL if the sensed ventricular activation is recognized as a VSI.

In Example 21, the subject matter of any one or more of Examples 19-20 optionally includes increasing the HBP pacing interval if the sensed ventricular activation is recognized as a VSH, and decreasing the HBP pacing interval if the sensed ventricular activation is recognized as a VSI.

In Example 22, the subject matter of any one or more of Examples 19-21 optionally includes determining a ventricular activation pattern including one or more previous ventricular activations followed by the recognized sensed ventricular activation, the one or more previous ventricular activations each including a VSI, a VSH, or a ventricular paced (VP) event, and determining one or more of the respective weight factors for the previous HBP pacing rate and for the measured VCL using the determined ventricular activation pattern.

This Overview is an overview of some of the teachings of the present application and not intended to be an exclusive or exhaustive treatment of the present subject matter. Further details about the present subject matter are found in the detailed description and appended claims. Other aspects of the disclosure will be apparent to persons skilled in the art upon reading and understanding the following detailed description and viewing the drawings that form a part thereof, each of which are not to be taken in a limiting sense. The scope of the present disclosure is defined by the appended claims and their legal equivalents.

BRIEF DESCRIPTION OF THE DRAWINGS

Various embodiments are illustrated by way of example in the figures of the accompanying drawings. Such embodiments are demonstrative and not intended to be exhaustive or exclusive embodiments of the present subject matter.

FIG. 6 is a block diagram illustrating an example of a method for adjusting an HBP configuration during AT to regularize ventricular rate during AT.

DETAILED DESCRIPTION

Figure 1:
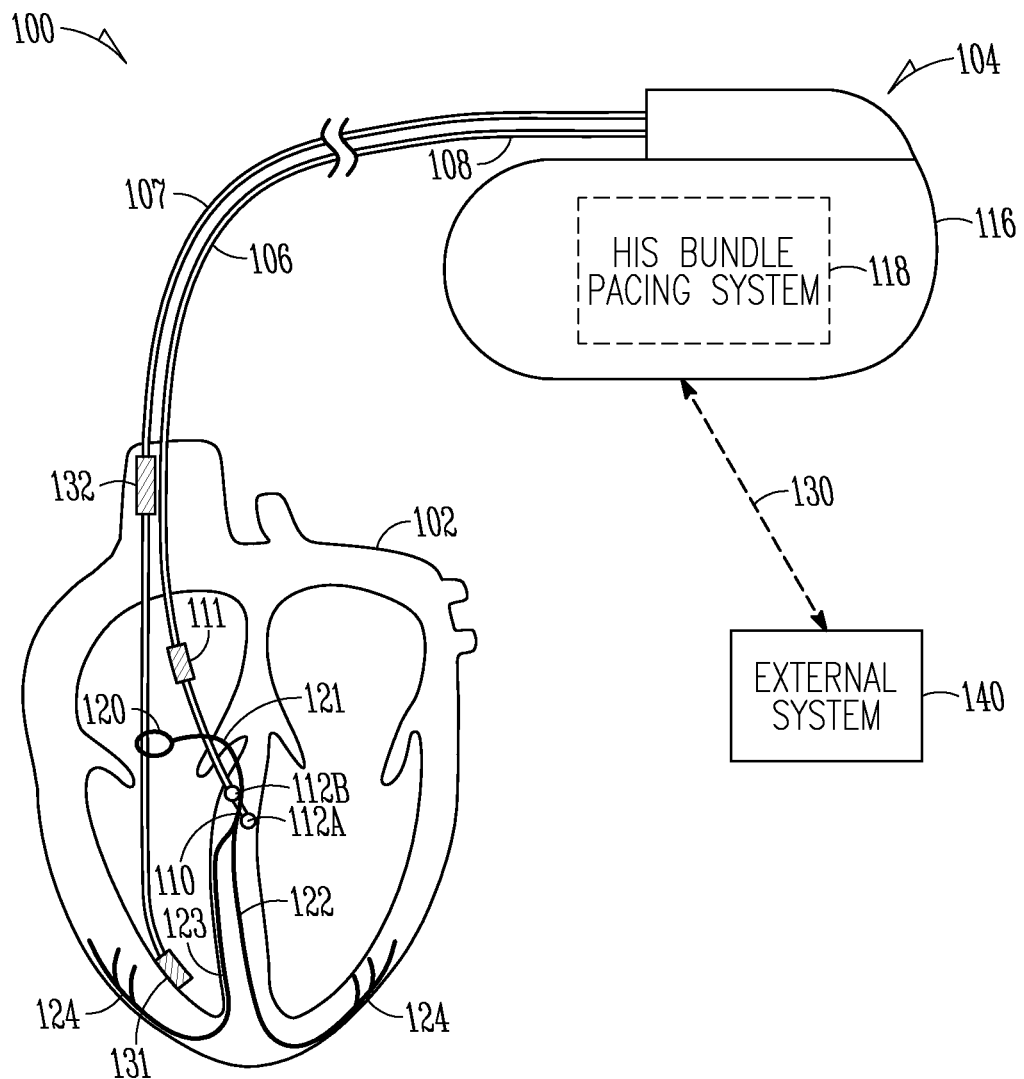
FIG. 1 illustrates generally an example of a cardiac disease management system and portions of an environment in which the system may operate.

Hemodynamic response to artificial pacing may depend on many factors, including pacing site selection and pacing configurations. Many patients receiving artificial pacing therapy have an intact His bundle and the natural cardiac electrical conduction system in the ventricles, therefore having normal ventricular activation. Conventional cardiac pacing such as long-term RV apex pacing may cause a decrease in cardiac efficiency due to the uncoordinated contraction sequence, and eventually exhibit adverse long-term effects. Ventricular dyssynchrony during conventional right ventricular pacing because the activation sequence may be much slower and propagate slowly from the right to the left ventricle across the interventricular septum, thereby causing ventricular dyssynchrony. This sequence of activation results in uncoordinated contraction, which does not occur during biventricular activation through the natural conduction system of the heart. The cells of the natural conduction system may propagate an activation signal about four times faster than working myocardium. A cardiac rhythm or functional management device configured to pace the His bundle is an alternative to conventional ventricular pacing in some patients. His-bundle pacing (HBP) may activate the heart's natural His-Purkinje system in some patients, and produce efficient and coordinated cardiac contractions. The potentially long-term harmful hemodynamic effects that may occur from continuous RV apex pacing may also be eliminated or reduced.

Cardiac pacing system, such as a pacemaker, have been used to manage atrial tachyarrhythmia (e.g., AF) and reduce patient symptoms. Various ventricular pacing regimens have been proposed to achieve rate control, either alone or in combination of pharmacological agents, by stabilizing or regularizing the ventricular rate, thereby avoiding AV nodal ablation. For example, right ventricular (RV) pacing in a VVI pacing mode have been used at a rate that results in a substantial percentage of depolarizations resulting from ventricular pacing, and a smaller percentage of depolarizations resulting from intrinsic conduction. Acute hemodynamic studies have revealed that such ventricular overdrive pacing may regularize the ventricular rate and improve cardiac performance. However, some clinical studies have demonstrated modest long-term improvement in patient symptoms, quality of life, or functional capacity. Similarly, ventricular rate control and regularization by AV nodal ablation and pacemaker implantation also fails to improve exercise capacity and quality of life in patients with AF compared with rate-control only with AV nodal blocking agents. This may be due to deleterious effects of long-term RV pacing, particularly RV apex pacing, which offset any potential benefit of ventricular rate regularization during AF.

For at least the above reasons, the present inventors have recognized that there is an unmet need for improved techniques of device-based ventricular rate control in AF while minimizing long-term structural and functional impairment to the heart attributed to RV overdrive pacing. Disclosed herein are systems, devices, and methods for pacing cardiac conductive tissue for rate control during atrial tachyarrhythmia. An embodiment of the system includes an electrostimulation circuit to generate HBP pulses to stimulate a physiologic conduction pathway, such as a His bundle or a bundle branch. An arrhythmia detector may detect an AT episode with intermittent ventricular conduction. A control circuit may sense ventricular activation and, in response to the detected AT indication, determine an HBP configuration using the sensed ventricular activation. HBP may be delivered according to the determined or adjusted HBP configuration to regularize His bundle activation rate and thus the ventricular rate during the AT.

The systems, devices, and methods discussed in this document may improve the technology of cardiac pacing in patients with cardiac disease, such as heart failure and AT. HBP may activate natural His-Purkinje system, thereby preserving ventricular synchrony and improving cardiac performance without structural and functional impairment to the heart. Among other aspects, the present document describes HBP according to a specific pacing paradigm to stimulate a His bundle or other parts of a physiologic conduction pathway to stabilize ventricular rate, and achieve ventricular rate control during AT, such as an atrial fibrillation (AF) or an atrial flutter (AFL) episode. Compared to conventional ventricular rate control in AF via RV overdrive pacing, HBP leverages the electrophysiology of the His bundle region and improves cardiac synchrony by utilizing the natural conduction mechanisms of the heart, thereby alleviating the long-term harmful hemodynamic effect associated with RV apex pacing and preserving the left-ventricular function. HBP-based ventricular rate regularization (VRR) may be more efficient and effective in achieving ventricular rate control than conventional VRR via RV pacing. In some examples, the system and methods discussed herein may distinguish between ventricular activation as a result of captured and conducted HBP and intrinsically conducted ventricular activation due to atrial impulses, and determine an HBP configuration (e.g., pacing rate or timing of HBP pulses) according to the distinguished ventricular activation. This may reduce the amount of HBP pulses delivered, improve overall HBP efficiency, and improve ventricular performance. The reduced amount of HBP may help conserve battery power and extend device longevity. With more effective VRR and improved cardiac performance, fewer unnecessary medical interventions, such as drugs, procedures, or device therapies, may be scheduled, prescribed, or provided to manage AT or heart failure symptoms. As a result, overall system cost savings may be realized.

While His-bundle pacing is specifically discussed in this document, this is meant only by way of example and not limitation. It is within the contemplation of the inventor, and within the scope of this document, that the systems, devices, and methods discussed herein may be applied to stimulate right or left bundle branches or fascicles, the Purkinje fibers, among other conductive cardiac tissue.

FIG. 1 is a schematic diagram illustrating an embodiment of a cardiac disease management system 100 and portions of an environment in which the system 100 may operate. The cardiac disease management system 100 may perform a range of activities, including remote patient monitoring, diagnosis of a disease condition, and providing a therapy to treat the disease condition and to improve patient outcome. In an example, the therapy may include His-bundle pacing (HBP). One or more of these activities may be performed proximal to a patient (e.g., in the patient's home or office), through a centralized server (e.g., in a hospital, clinic or physician's office), or through a remote workstation (e.g., a secure mobile computing device).

As illustrated in FIG. 1, the cardiac disease management system 100 may be coupled to a patient's heart 102. The cardiac disease management system 100 includes an ambulatory medical device (AMD) and a lead system, configured to treat one or more cardiac diseases, such as cardiac arrhythmias or heart failure. The AMD may be an implantable device subcutaneously implanted in a chest, abdomen, or other parts of the patient, a subcutaneous monitor or diagnostic device, or a wearable medical device such as a patch-based device or a smart wearable or accessory, among others. In the example as illustrated in FIG. 1, the AMD includes an implantable medical device (IMD) 104. Examples of the IMD 104 may include a pacemaker, a pacemaker/defibrillator, a cardiac resynchronization therapy (CRT) device, a cardiac remodeling control therapy device, a neuromodulator, a drug delivery device, a biological therapy device, or an implantable diagnostic device such as a cardiac monitor or a loop recorder, among other implantable devices.

The lead system may include one or more transvenously, subcutaneously, or non-invasively placed leads or catheters. Each lead or catheter may include one or more electrodes. The arrangements and uses of the lead system and the associated electrodes may be determined by patient need and capability of the IMD 104. The associated electrodes on the lead system may be positioned at the patient's thorax or abdomen to sense a physiological signal indicative of cardiac activity, or a physiological response to stimulation of a target tissue. The lead system may be surgically inserted into, or positioned on the surface of, a heart 102. The electrodes associated with the lead system may be disposed in a target site in a right atrium (RA), a right ventricle (RV), a left atrium (LA), or a left ventricle (LV), or other body parts. Stimulation energy may be delivered to a target site via one or more of these electrodes. Some electrodes may be used for sensing cardiac activity, such as an intrinsic or evoked cardiac electrical activity.

In the illustrated example, the lead system may include a lead 106 having a proximal end 108 configured to be connected to the IMD 104, and a distal end 110 that includes one or more electrodes configured to deliver stimulation energy, such as in a form of pacing pulses, to the His bundle 121. FIG. 1 illustrates, by way of example and not limitation, two electrodes including a tip electrode 112A and a ring electrode 112B. Additional electrodes may be included in the lead 106 for sensing electrical activity or for delivering stimulation energy. The lead 106 may be placed such that one or more electrodes, such as 112A-112B, are positioned in or on a His bundle 121, a region distal to the blocked or slowly conducting AV node and in the AV septum, an interventricular septum region, or a right atrial region near the His-bundle 121. Alternatively, one or more of the electrodes 112A-112B, or other electrodes on the lead 106, may be configured to stimulate a bundle branch, such as a left bundle branch or a right bundle branch. As part of the natural electrical conduction system of the heart 102, the His bundle 121 transmits the electrical impulses from the AV node 120 to the point of the apex of the fascicular branches via the left bundle branch 122 and the right bundle branch 123. Each of the left and right branch bundles leads to the Purkinje fibers 124, which provide electrical conduction to the ventricles, causing the ventricles to contract. In some examples, the lead 106 may be placed such that one or more electrodes associated with the lead 106, such as 112A-112B, are positioned at or near other parts of the natural conduction pathways, such as one of the bundle branches 122 or 123, the Purkinje fibers 124, or other conductive tissue, in addition to or in lieu of a region at or near the His bundle 121.

In an example, the lead 106 may be a single pass lead having a plurality of electrodes for stimulating multiple cardiac sites, including electrodes disposed at or near the His bundle (e.g., the electrodes 112A-112B) and electrodes disposed in one or more of RA, RV, LA, or LV of the heart 102. In some examples, in addition to the lead 106, the lead system may include separate leads for placement in different heart chambers or sites, such as an RA lead having one or more RA electrodes to stimulate a portion of RA or to sense RA electrical activity, a RV lead having one or more RV electrodes to stimulate a portion of RV or to sense RV electrical activity, or an LV lead having one or more LV electrodes to stimulate a portion of LV or to sense LV activity. In some examples, the cardiac disease management system 100 may include one or more leadless stimulators/sensors untethered to a lead and in wireless communication with the IMD 104. The leadless stimulators/sensors may deliver electrostimulation, sense a physiological signal, such as cardiac electrical signals in response to cardiac stimulation, and transmit the sensed data to the IMD 104.

The IMD 104 may include a hermetically sealed housing 116 that houses one or more of an electrostimulation circuit, a sensing circuit, a control circuit, a communication circuit, and a battery, among other components. In an example, the IMD 104 includes a His-bundle pacing system 118 configured to generate His-bundle pacing (HBP) pulses to stimulate the His bundle 121, such as via the lead 106 and the associated electrodes 112A or 112B. The His-bundle pacing system 118 may be programmed to deliver unipolar His-bundle pacing, where the pacing energy (current or voltage) is applied between one of the electrodes 112A-112B (e.g., as a cathode) and the housing 116 (e.g., as an anode). Alternatively, the His-bundle pacing system 118 may be programmed to deliver bipolar His-bundle pacing, where the pacing energy (current or voltage) is applied between two electrodes positioned at or near the His bundle, such as between the electrodes 112A and 112B. In some examples, electrodes used for unipolar or multipolar (e.g., bipolar or quadripolar) His-bundle pacing may be selected by a system user from a plurality of candidate electrodes from a given lead or multiple separate leads comprising the pacing system, and programmed into the His-bundle pacing system 118. In some examples, HBP pulses may be provide by a leadless device, such as a leadless cardiac pacemakers (LCP). One or more electrodes may be distributed on the body of the LCP and in contact with His-bundle region to deliver the HBP pulses.

The His-bundle pacing system 118 may sense a physiological signal using one or more electrodes associated with the lead system or a physiological sensor. Examples of the physiological signal may include an electrocardiogram (ECG), an intracardiac electrogram (EGM) such as an atrial EGM, a ventricular EGM, or a His bundle EGM, an thoracic impedance signal, a cardiac impedance signal, an arterial pressure signal, a pulmonary artery pressure signal, a left atrial pressure signal, an RV pressure signal, an LV coronary pressure signal, a coronary blood temperature signal, a blood oxygen saturation signal, a heart sound signal, an intracardiac acceleration signal, a respiration signal, or a physical activity or exertion level signal, among others. In some examples, the His-bundle pacing system 118 may sense far-field ventricular activation (FFVA) using one or more electrodes or a physiologic sensor. The FFVA may be a signal recorded from afar at a given moment in time by two electrodes having similar source impedance. The FFVA may be sensed in response to electrostimulation to the His bundle or a bundle branch. In an example, the FFVA includes an EGM sensed via an electrode positioned within, or on the epicardial surface of, a ventricle. In an example as illustrated in the FIG. 1, the lead system may include a ventricular lead 107 including at least one RV electrode 131, which may be a tip electrode, a ring electrode, or a coil electrode. The His-bundle pacing system 118 may sense a FFVA signal (e.g., a far-field EGM) using the RV electrode 131 (e.g., as a cathode) and a reference electrode (e.g., as an anode). The EGM sensed as such using an RV electrode represents far-field LV activation, or far-field BiV activation. In an example, the reference electrode is a proximal electrode 132 on the ventricular lead 107. The proximal electrode 132 may be a coil electrode situated at the superior vena cava (SVC) of the heart. The distal electrode 131 and the proximal electrode 132 may also be used to deliver defibrillation shocks to correct ventricular tachyarrhythmia. In an example, the reference electrode may include the housing 116 or an electrode therein. In another example, the FFVA signal may be sensed using an atrial electrode 111 associated with the lead 106 and positioned in the RA and a reference electrode. In yet another example, the FFVA signal may be sensed using a His-bundle electrode associated with the lead 106 (e.g., electrode 112A or 112B) and a reference electrode. Examples of the reference electrode may include the housing 116 or an electrode therein. In another example, the FFVA signal may include a subcutaneous ECG signal sensed using subcutaneous chest electrodes such as located at the housing 116. In yet another example, the FFVA signal may include surface ECG signal sensed using skin electrodes attached to the body surface.

The His-bundle pacing system 118 may include electrostimulation circuitry that stimulate a patient physiologic conduction pathway (e.g., His bundle or a part of a bundle branch) to regularize ventricular rate during atrial tachyarrhythmia (AT), thus improving cardiac hemodynamics through ventricular rate control during AT. To achieve desired ventricular rate regularization (VRR), the His-bundle pacing system 118 includes a control circuit that may determine or adjust a HBP configuration using ventricular activation information. Examples of the HBP configuration may include a pacing rate, a pacing interval, or timing for HBP pulses delivery, among others. The ventricular activation information may include ventricular rate, interval, or activation timing, which may be extracted from the sensed physiologic signal. In an example, the His-bundle pacing system 118 may detect an AT indication with intermittent ventricular conduction, and dynamically adjust the HBP configuration. In some examples, the His-bundle pacing system 118 may distinguish between ventricular activation caused by HBP that captures and conducts to the ventricles, and intrinsically conducted ventricular activation due to atrial activity, and determine a corresponding HBP configuration for the distinguished ventricular activation. The electrostimulation circuitry may stimulate the physiologic conduction pathway in accordance with the determined HBP configuration to regularize ventricular activation rate during AT. Examples of determining or adjusting HBP configuration to regularize ventricular rate during AT are discussed below, such as with reference to FIGS. 2-4.

The IMD 104 may communicate with an external system 140 via a communication link 130. The external system 140 may include a dedicated hardware/software system such as a programmer, a remote server-based patient management system, or alternatively a system defined predominantly by software running on a standard personal computer. The external system 140 may include a proximal external device such as a programmer device in proximity of the IMD 104. A clinician may manage the patient 102 through the IMD 104 via the communication link 130. This may include, for example, programming the IMD 104 to sense physiological signals, analyzing the physiological signals to detect a medical condition such as heart failure, assessing therapy efficacy, performing a self-diagnostic test, or initiating or adjusting a therapy such as HBP. Additionally, the external system 140 may receive device data from the IMD 104 via the communication link 130. Examples of the device data may include real-time or stored physiological signals collected from the patient 102, physiological response to therapies delivered to the patient 102, or device operational status of the IMD 104 (e.g., battery status and lead impedance). The communication link 130 may be an inductive telemetry link, a capacitive telemetry link, or a radio-frequency (RF) telemetry link, or wireless telemetry based on, for example, "strong" Bluetooth or IEEE 802.11 wireless fidelity "WiFi" interfacing standards. Other configurations and combinations of patient data source interfacing are possible.

The external system 140 may monitor patient condition and the function of IMD 104. In various embodiments, the external system 140 may include a user interface to display the received information to the user, and receive user input for operation control of the IMD 104. In an example, the external system 140 may be configured to verify pacing capture status, perform pacing threshold test to determine an HBP threshold. The capture verification and threshold testing may be executed periodically, or triggered by a specific event such as a user command. A user may use the external system 140 to program the IMD 104, such as to configure a pacing vector (e.g., specifying anode and cathode electrodes) to deliver HBP, or to configure a sense vector to sense a physiological signal.

The external system 140 may include a remote device in a location relatively distant from the IMD 104 and in communication with the proximal external device via a telecommunication network. The remote device may evaluate collected patient data and provide alert notifications, among other possible functions. In an example, the remote device may include a centralized server acting as a central hub for collected patient data storage and analysis. The server may be configured as a uni-, multi- or distributed computing and processing system. The server may include an alert analyzer circuit to evaluate the collected patient data to determine if specific alert condition is satisfied. Satisfaction of the alert condition may trigger a generation of alert notifications. In some examples, the alert conditions alternatively or additionally may be evaluated by the IMD 104. By way of example, alert notifications may include a Web page update, phone or pager call, E-mail, SMS, text or "Instant" message, as well as a message to the patient and a simultaneous direct notification to emergency services and to the clinician. Other alert notifications are possible. In various examples, the remote device may additionally include one or more locally configured clients or remote clients securely connected over the telecommunication network to the server. Examples of the clients may include personal desktops, notebook computers, mobile devices, or other computing devices. System users, such as clinicians or other qualified medical specialists, may use the clients to securely access stored patient data assembled in the database in the server, and to select and prioritize patients and alerts for health care provisioning.

The external system 140 may output the detected medical events or therapy efficacy information (such as capture verification or classification) to a system user such as the patient or a clinician, or to a process including, for example, an instance of a computer program executable in a microprocessor. In an example, the process may include an automated generation of recommendations for initiating or titrating a medical therapy or an electrostimulation therapy. In an example, the external device 120 or the remote device 124 may include a respective display unit for displaying the physiological signals, stimulation parameters, capture verification, or classification of capture types, among other intermediate analyses and computations. Alerts, alarms, emergency calls, or other forms of warnings to signal the detected medical event may also be generated.

Portions of the IMD 104 or the external system 140 may be implemented using hardware, software, firmware, or combinations thereof. Portions of the IMD 104 or the external system 140 may be implemented using an application-specific circuit that may be constructed or configured to perform one or more particular functions, or may be implemented using a general-purpose circuit that may be programmed or otherwise configured to perform one or more particular functions. Such a general-purpose circuit may include a microprocessor or a portion thereof, a microcontroller or a portion thereof, or a programmable logic circuit, a memory circuit, a network interface, and various components for interconnecting these components. For example, a "comparator" can include, among other things, an electronic circuit comparator that may be constructed to perform the specific function of a comparison between two signals or the comparator may be implemented as a portion of a general-purpose circuit that may be driven by a code instructing a portion of the general-purpose circuit to perform a comparison between the two signals.

Figure 2:
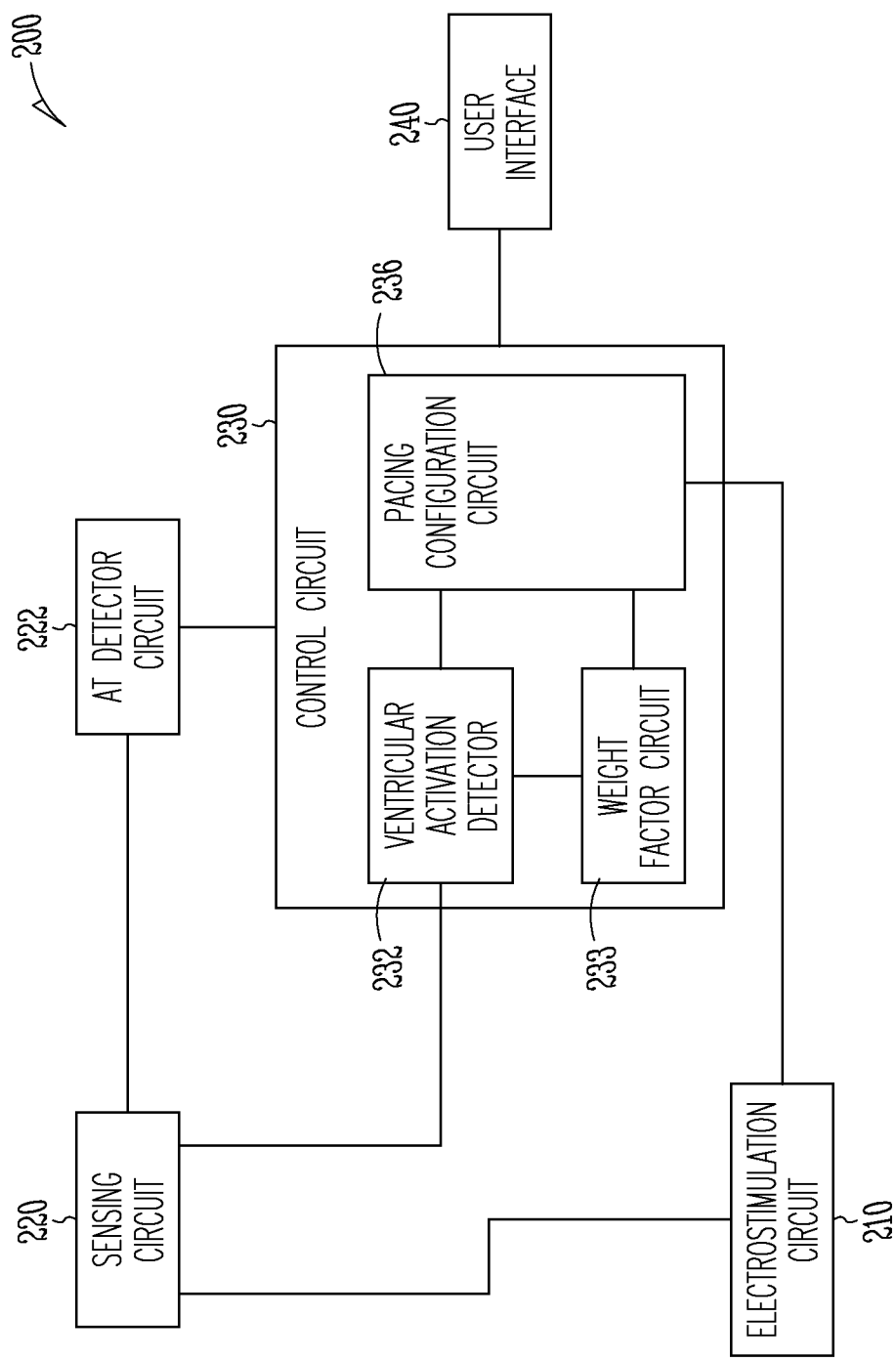
FIG. 2 is a block diagram illustrating an embodiment of portions of a His-bundle pacing system.

FIG. 2 is a block diagram illustrating an embodiment of portions of a His-bundle pacing system 200. The His-bundle pacing system 200 represents an embodiment of the His-bundle pacing system 118, and may include an electrostimulation circuit 210, a sensing circuit 220, an AT detector circuit 222, a control circuit 230, and a user interface 240.

The electrostimulation circuit 210 may be configured to generate stimulation energy for delivery to the heart 102, such as via one or more leads and the associated electrodes. The electrostimulation circuit 210 may be configured to generate His-bundle pacing (HBP) pulses for delivery to a target pacing site at or near the His bundle at or near the His bundle or a bundle branch along the conduction pathway, such as via the lead 106 and one or more of the electrodes 112A-112B. The target site may include an interventricular septum region or a right atrial region near the His-bundle, or other conductive tissue such as right or left bundle branches or fascicles, or Purkinje fibers. In an example, the HBP pulses may be delivered in multiple cardiac cycles, such that at least one pulse is delivered within each of the multiple cardiac cycles. In various examples, the electrostimulation circuit 210 may additionally generate electrostimulation to stimulate non-cardiac tissue, such as nerve tissue, muscle tissue, or other excitable tissue.

The electrostimulation circuit 210 may generate HBP pulses according to one or more stimulation parameters such as provided by control circuit 230. Examples of the stimulation parameters may include information about stimulation site, stimulation strength, stimulation mode, or stimulation timing, among other parameters. Stimulation site includes information about pacing site, pacing vector configuration (e.g., anode and cathode electrodes), unipolar or bipolar pacing, cardiac resynchronization therapy (CRT), BiV pacing, or synchronized left ventricle (LV)-only pacing, single site pacing of only one site of a heart chamber (e.g., the left ventricle), or multisite pacing (MSP) of two or more sites of a heart chamber within the same cardiac cycle (e.g., multisite LV pacing), among others. Stimulation strength parameters determine the amount of energy delivered to the pacing site, and may include pulse amplitude, pulse width, pulse frequency, pulse waveform, duty cycle, or stimulation duration. In some examples, the stimulation parameters may include one or more HBP parameters such as pacing rate, pacing interval, or timing of HBP pulses, among others parameters, which are collectively referred to as HBP configuration in this document.

Stimulation mode includes, by way of example and not limitation, a His-bundle only mode, an atrial-Hisian (AH) pacing mode, a His-ventricular (HV) pacing mode, or an atrial-His-ventricular (AHV) pacing mode. In the His-bundle only pacing mode, atrial activation may be sensed by the His-bundle pacing electrode, such as by using a single pass lead, or a leadless pacemaker having a form factor with multiple electrodes positioned such that reliable atrial sensing may be achieved. In the AH pacing mode, the HBP pulses may be delivered only when intrinsic atrial activation (AS), or atrial pacing (AP), fails to produce propagatable depolarization of the AV node and the His bundle. The AH pacing mode may be suitable for patients with varying degrees of heart block or sick sinus syndrome. The HV pacing mode involves sequential pacing of the His bundle and the ventricle. The ventricular pacing may be provided in a demand mode, such that the ventricular pacing pulses are delivered only when the His pacing fails to produce propagatable depolarization of the ventricles. The HV pacing mode may be indicated for patients with persistent or chronic atrial fibrillation, or who have been treated with atrioventricular node ablation or drugs to slow and the rapid ventricular rhythm that often results and allow HBP to predominate. The AHV pacing mode involves sequential atrial, Hisian, and ventricular pacing. One or more of the His-bundle pacing or the ventricular pacing may be delivered in a demand mode. The AHV pacing mode may be indicated for patients with cardiac dyssynchrony and having received cardiac resynchronization therapy, patients suffering from HF with LBBB, HF induced by right ventricular pacing, long PR intervals with hemodynamic compromise, or pacemaker induced cardiomyopathy from conventional dual-chamber pacing.

Stimulation timing parameters determine the timing and sequence of pacing pulses. For example, in demand AH pacing mode, the HBP pulses are timed relative to an AS or an AP event. An AH timing represents a latency period, within a cardiac cycle, from an intrinsic AS event or an AP event to the delivery of an HBP pulse. In demand HV pacing mode, the ventricular pacing pulses are timed relative to a His pacing event. The HV timing represents a latency period, within a cardiac cycle, from a His bundle event (e.g., an HBP pulse) to the delivery of ventricular pacing pulse. In an example, if an HBP pulse fails to induce ventricular depolarization, a backup ventricular pacing may be delivered at the end of the HV timing. The stimulation timing parameters may additionally include parameters associated with CRT or MSP therapy, such as atrial-ventricular delay (AVD) representing a latency period from an AS or AP event to ventricular pacing, an RV-LV interventricular pacing delay (VVD) representing a time delay between ventricular pacing at the left and right ventricles, or intra-ventricular pacing delay representing a time delay between pacing at multiple site of a ventricle.

The electrostimulation circuit 210 may be configured to provide selective pacing at a site with only a targeted tissue being directly excited, without substantial unintended and undesirable excitation of other non-targeted tissue. If the pacing directly causes intended excitation of the targeted tissue as well as unintended excitation of other non-targeted tissue, a non-selective pacing results. In the context of HBP, selective HBP causes only the excitation (depolarization) of the His bundle, without direct excitation of para-Hisian myocardium adjacent to the His bundle. Non-selective HBP directly causes excitation of both the His bundle and the para-Hisian myocardium. If the HBP pulses cause only excitation of the para-Hisian myocardium or other unintended cardiac tissue, without direct excitation of the His-bundle fibers, then a para-Hisian pacing results. If no tissue excitation is induced by HBP (e.g., neither the para-Hisian myocardium capture nor the His-bundle capture), then a complete loss of capture (LOC) results.

The electrostimulation circuit 210 may generate backup pacing pulses for delivery to the heart to excite the myocardium and prevent asystole. The backup pacing pulses may be delivered when a loss of capture is produced, or alternatively when para-Hisian capture is produced. The backup pacing may be delivered to a target ventricular site via a lead with associated electrodes disposed in or on a ventricle, such as a right ventricle. Additionally or alternatively, the backup pacing may be delivered to the His bundle, such as the site for delivering HBP pulses, via the same His-bundle pacing lead with associated electrodes. In an example, the backup pacing may include high-output pacing (HOP) pulses with higher pacing energy than conventional pacing pulses. The HOP pulse may be a biphasic or multiphasic waveform. In an example, the HOP pulse may have a peak-to-peak voltage amplitude of 5-8 volts, and a pulse duration of 50-70 msec. With higher amount of energy delivered to the myocardium, the HOP pulse may increase myocardial contractility and improve systolic function. However, chronic HOP pacing may overstress the heart and potentially be hazardous in some heart failure patients. According, in some examples, the HOP pulses may be delivered on an intermittent basis, such that the conventional pacing pulses are delivered in 3-5 cardiac cycles between the HOP pulses. In an example, the HOP pulses may be delivered when one or more physiologic sensors sense a deterioration in cardiac hemodynamics, in addition to the indication of loss of capture of para-Hisian capture. Arcot-Krishnamurthy et al. U.S. Pat. No. 8,588,907, entitled "CLOSED-LOOP CONTROL OF INTERMITTENT EXCITATORY CARDIAC STIMULATION FOR THERAPEUTIC EFFECT," refers to high-output pacing that is excitatory and of sufficient energy to augment myocardial contractility, which is incorporated herein by reference in its entirety.

The sensing circuit 220 may be coupled to one or more electrodes or physiologic sensors to sense a physiologic signal indicative of a response of a portion of the heart 102 to the delivery of HBP pulses. Examples of the sensed signals may include an electrocardiogram (ECG), an electrogram (EGM) of a portion of the heart such as atrial EGM, ventricular EGM, or evoked His potential, an impedance signal, a heart sound signal, or a pressure signal, among other physiological or hemodynamic signals indicative of a tissue response to the delivery of HBP pulses. In various examples, the sensing circuit 220 may sense a far-field ventricular activation (FFVA) signal. The FFVA signal may include a far-field electrical signal (e.g., an electrogram) indicative of electrical synchrony of depolarizations of the left and right ventricles in response to the HBP delivery. The far-field EGM may be sensed using a unipolar or a bipolar configuration. In an example, the far-field EGM may be sensed via a ventricular electrode positioned within or on the epicardial surface of an RV or LV, such as the distal electrode 131 on the ventricular lead 107 as shown in FIG. 1. In various examples, the far-field EGM may be sensed between the ventricular electrode 131 and the proximal electrode 132, between the ventricular electrode 131 and the housing 116 or an electrode therein, or between the ventricular electrode 131 and a joint electrode comprising the proximal electrode 132 and the housing 116 or an electrode therein that are at least temporarily electrically tied together. Such far-field EGMs sensed using the ventricular electrode 131 may represent far-field LV or far-field BiV (i.e., LV and RV) activations, as well as ventricular synchrony as manifested by QRS width or interventricular conduction delay. Additionally or alternatively, the FFVA may be sensed using electrodes positioned in or on other heart chambers or locations other than RV and LV. In an example, the FFVA may be sensed using an atrial electrode, such as the RA electrode 111 associated with the lead 106, and a reference electrode such as the housing 116 or an electrode therein. In yet another example, the FFVA may be sensed using electrodes positioned in or on a His-bundle region, such as one of the electrodes 112A-112B associated with the lead 106, and a reference electrode such as the housing 116 or an electrode therein. In yet another example, the FFVA signal may include a subcutaneous ECG signal sensed using chest electrodes such as located at the housing 116. Such FFVA may contain information about ventricular synchrony, such as QRS width or interventricular conduction delay.

In some examples, the FFVA signal may include a mechanical signal indicative of mechanical synchrony of contractions and vibrations between of the left and right ventricles. Examples of the mechanical signal may include an impedance signal, a heart sound signal, a pressure signal, among other hemodynamic signals that may be sensed using a physiologic sensor.

The AT detector circuit 222 may be configured to detect an AT indication, such as an indicator of an AF or AFL event with intermittent ventricular conduction. Irregular ventricular rates due to AT may cause patient discomfort, decrease cardiac output, increase susceptibility to ventricular tachyarrhythmia, deteriorate cardiac hemodynamic function, and exacerbate heart failure status. The AT detector circuit 222 may detect the AT indication using information of cardiac activities at one or more cardiac chambers or cardiac sites. In an example, the AT indication may be detected using atrial activation information, such as an atrial EGM sensed via the atrial electrode 111 associated with the lead 106, or the supraventricular SVC electrode 132 associated with the lead 107. Atrial rate may be determined using the sensed atrial activity, and an AT indication may be detected if the atrial rate exceeds an atrial rate threshold. In another example, the AT indication may be detected using ventricular activation information, such as a ventricular EGM sensed via the distal ventricular electrode 131 associated with the lead 107, or a FFVA signal as discussed above. Ventricular rate and rate stability (e.g., variance, standard deviation, inter-beat cycle length difference, or other statistical measures of variability) may be determined from the sensed ventricular activity. In an example, an AT indication may be detected if the ventricular rate stability exceeds a stability threshold. In yet another examples, the AT indication may be detected using activation of a portion of the physiologic conduction pathway, such as His-bundle activation or bundle branch activation. During an AT episode, atrial impulses may be intermittently conducted to the ventricle. The intermittent conduction pattern may be sensed at the His-bundle or the bundle branch, such as using one or more of the His-bundle electrodes 112A or 112B. The His-bundle rate and rate stability (e.g., variance, standard deviation, inter-beat cycle length difference, or other statistical measures of variability) may be determined using the sensed His-bundle activity, and an AT indication may be detected if the His-bundle rate stability exceeds a stability threshold.

In an example, the AT detector circuit 222 may detect the AT indication using a change in pacing statistics. In an instance of physiologic pacing (e.g., pacing the physiologic conduction pathway such as His-bundle or a bundle branch) to restore or improve cardiac synchronization, a high atrial rate during AT may increase the amount and frequency of atrial impulses that conduct and activate the ventricles. Consequently, fewer HBP pulses would be delivered to activate the ventricles. Accordingly, a decrease in the amount of HBP pulses being delivered may be suggestive of a presence of AT The AT detector circuit 222 may monitor the frequency of HBP delivery (e.g., a number of HBP pulses being delivered within a specified time period), and detect the AT indication when the frequency of HBP delivery falls below a specific HBP frequency threshold.

In an example, the AT detector circuit 222 may detect the AT indication using a change in pacing mode. For example, a pacing system may have an atrial tachy response (ATR) parameter and mode switch feature. When the atrial rate is sufficiently high (e.g., exceeds an atrial rate threshold) and sustains for a specific time period or a specific amount of beats (e.g., exceeding a duration or beat count threshold), the ATR feature may be activated, switching the cardiac pacing (e.g., ventricular pacing) from an atrial tracking mode (e.g., DDD(R) or VDD mode) to a non-tracking mode (e.g., DDI(R) or VDI(R) mode) in which ventricular pacing is irrespective of atrial sensed events. The mode switch may prevent rapid ventricular pacing in the presence of AT. Because the triggering of ATR and the automatic mode switch is an indication of occurrence of an AT episode, in an example, the AT detector circuit 222 may detect the AT indication using a transition from an atrial tracking-mode to a non-atrial tracking mode. When the pacing mode falls back to the tracking mode, the AT episode likely terminates.

The control circuit 230 may determine an HBP configuration in the presence of AT, and control the delivery of HBP pulses in accordance with the determined HBP configuration to stabilize ventricular activation during AT. In an example, the control circuit 230 may be implemented as a part of a microprocessor circuit in the cardiac disease management system 100. The microprocessor circuit may be a dedicated processor such as a digital signal processor, application specific integrated circuit (ASIC), microprocessor, or other type of processor for processing information including heart sounds. Alternatively, the microprocessor circuit may be a general-purpose processor that may receive and execute instructions of performing the functions, methods, or techniques described herein.

As illustrated in FIG. 2, the control circuit 230 may include circuit sets comprising a ventricular activation detector circuit 232, a weight factor circuit 233, and a pacing configuration circuit 236. These circuits, alone or in combination, perform the functions, methods, or techniques described herein. In an example, hardware of the circuit set may be immutably designed to carry out a specific operation (e.g., hardwired). In an example, the hardware of the circuit set may include variably connected physical components (e.g., execution units, transistors, simple circuits, etc.)

including a computer readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuit set in hardware via the variable connections to carry out portions of the specific operation when in operation. Accordingly, the computer readable medium is communicatively coupled to the other components of the circuit set member when the device is operating. In an example, any of the physical components may be used in more than one member of more than one circuit set. For example, under operation, execution units may be used in a first circuit of a first circuit set at one point in time and reused by a second circuit in the first circuit set, or by a third circuit in a second circuit set at a different time.

The ventricular activation circuit 232 may receive information of ventricular activation, such as ventricular beats. In an example, the ventricular activation circuit 232 may be coupled to the sensing circuit 220, and extract the information of ventricular activation from the sensed physiologic signal, such as ventricular EGM, the FFVA signal, or cardiac mechanical signals. In another example, the ventricular activation information may be collected from a patient and stored in a data storage device such as an electronic medical record system, and the ventricular activation circuit 232 may access the ventricular activation information. The ventricular activation circuit 232 may detect ventricular beats within a sensing window, and determine ventricular cycle length and/or ventricular heart rate. The ventricular cycle length or ventricular heart rate may be used to determine or adjust an HBP pacing configuration.

The pacing configuration circuit 236 may determine or adjust an HBP configuration in response to the AT indication, such as produced by the AT detector circuit 222, which indicates presence of an AT episode with irregular ventricular rates. The HBP configuration may include pacing parameters such as HBP pacing interval (HPI), pacing rate, or timing of HBP pulses. HBP delivered in accordance with the determined HBP configuration may regularize His bundle activation and hence regularize ventricular rate during AT. In an example, the pacing configuration circuit 236 may adjust the HBP configuration on a beat-by-beat basis using the detected ventricular beats. In an example, the HPI may be updated recursively using a combination of a previously determined HPI and a ventricular cycle length (VCL) corresponding to the presently detected beat. The combination may be a linear or a nonlinear combination. Equation (1) below is an example of such a recursive update HPI using a weighted combination of a previous HPI and the present VCL each scaled by respective weight factors:

$$HPI(n)=a*HPI(n-1)+b*VCL(n) \quad (1)$$

where HPI(n) represents the recursively updated HBP pacing interval (in seconds or milliseconds) corresponding to the present ventricular beat "n", HPI (n−1) represents previously determined HBP pacing interval corresponding to ventricular beat "n−1", and VCL(n) represents the ventricular cycle length of the present ventricular beat "n". In an example, the HBP pulse is timed relative to a reference time, such as a ventricular sensed event (VS) or an atrial sensed event (AS). The HPI determined according to Equation (1) above then determines or updates timing of HBP pulse relative to the reference time. In another example, the HBP pulse is timed relative to the immediate previous HBP pulse. The HPI determined according to Equation (1) then represents interval between HBP pulses, or equivalently the HBP pulse rate (HPR) as determined by HPR=60/HPI.

The weight factor circuit 233 may determine the weight factors "a" and "b" in Equation (1). These weight factors respectively control the influence of past HPI and the presently sensed VCL. In an example, the weight factors "a" and "b" are user specified scalars between 0 and 1. Because "a" is less than 1, the HPI (n) may be less than HPI (n−1), such that the HBP pacing interval may be gradually reduced (or the HBP pacing rate is gradually increased) during AT. However, the influence of past HPI may be tempered by the previous history. In some examples, as an alternative to programming the weight factors "a" and "b" to respective numerical values, a user may program a categorical value, such as "min", "medium", or "max" for the weight factors. The categorical values represent different degrees of sensitivity and correspond to respective numerical value ranges for the weight factors. A higher setting (e.g., "max") corresponds to an increased HBP frequency (i.e., shorter HPI and more HBP pulses being delivered) and lower ventricular rate variability compared to a lower setting (e.g., "min").

In some examples, the weight factor circuit 233 may determine one or more of the weight factors "a" and "b" based on a ventricular event type, such as either a ventricular response to the HBP pulses ($VS_H$) that capture the His-bundle and conduct to the ventricles, or an intrinsically conducted ventricular activation ($VS_I$) due to atrial activations during AT. Distinguishing between $VS_H$ and $VS_I$ events and determining accordingly the HBP configuration (e.g., HPI) may help reduce HBP delivery, improve overall HBP efficiency, and enhance ventricular performance. In some examples, the weight factor circuit 233 may alternatively or additionally determine one or more of the weight factors "a" and "b" based on a ventricular event pattern, such as a sequence of sensed ventricular events of the same or different types. Examples of determining weight factors using ventricular event type or ventricular event pattern and updating the HBP configuration accordingly are discussed below, such as with reference to FIGS. 3A-3B.

In some examples, the recursively determined HPI according to Equation (1) may be bound by a lower rate limit (LRL) and a maximum pacing rate (MPR), that is, LRL≤HPR≤MPR. The LRL represents a base rate above which the HBP is initiated in the absence of sensed intrinsic cardiac activity or sensor-controlled pacing at a higher rate. The LRL may be programmable, such as between 50-150 beats per minute (bpm). In an example, the LRL may be set to approximately 60 bpm. The MPR limits the maximum His-bundle pacing rate that the recursively determined HPR may reach. The MPR may be programmable, such as between 60-150 bpm. In an example, the MPR may be set to approximately 110 bpm.

The user interface 240 may include an input unit and an output unit. At least a portion of the user interface 240 may be implemented in the external system 140. The input unit may receive user input such as values of the parameters for physiologic event sensing, atrial tachyarrhythmia detection, thresholds for His bundle capture verification, discrimination between different types of ventricular event types (e.g., $VS_H$ and $VS_I$ events), among others. The user input may receive user programming of stimulation parameters, or confirmation, rejection, or otherwise modification of the parameters generated by the pacing configuration circuit 236 such as HBP pacing intervals, pacing rates, or timing of HBP pulse delivery. In an example, the user may program the weight factors for the previous HBP pacing rate and for the measured VCL to specific numerical values or categorical values. The input unit may include an input device such as a keyboard, on-screen keyboard, mouse, trackball, touchpad, touch-screen, or other pointing or navigating devices.

The output unit may include circuitry configured to generate a human-perceptible notification of the detected AT and HBP configuration determined by the pacing configuration circuit 236. The output unit may be coupled to a display for displaying the received physiologic signals (e.g., ECG, EGMs, FFVA signals, or cardiac mechanical activity signals), event sensing information such as ventricular event types (e.g., $VS_H$, $VS_I$, or VP events) and event timings, ventricular event patterns, etc. The event sensing information may be overlaid with the signal tracings, or be displayed in a separate marker channel. The stimulation parameters, and intermediate measurements or computations may also be displayed. The output unit may be coupled to a printer for printing hard copies of information about the event detection and therapy titration protocol. The information may be presented in a table, a chart, a diagram, or any other types of textual, tabular, or graphical presentation formats. The presentation of the output information may include audio or other media formats. In an example, the output unit may generate alerts, alarms, emergency calls, or other forms of warnings to signal the system user about the His-bundle capture status, onset and termination of an AT episode, restoration of ventricular rate stability, among others. In an example, the output unit may generate an alert when a loss of capture is indicated and a backup pacing is delivered. In another example, frequent backup pacing delivery may trigger the output unit to generate an alert and prompt a user (e.g., a clinician) to reprogram the pacing system.

Portions of the His-bundle pacing system 200 may be implemented distributedly between two devices. In an example, a first device may include the electrostimulation circuit 210 and a stimulation delivery system (e.g., a pacing lead and associated electrodes for delivering HBP pulses, or an untethered pacing unit for delivering HBP pulses), and a second device may include the sensing circuit 220 and at least a portion of the control circuit 230. The sensing circuit 220 of the second device may be configured to sense, among other signals, the far-field ventricular response to the HBP pulses. In an example, the first and second devices are both implantable devices. In another example, at least one of the first or the second device is a non-implantable, wearable device.

Figure 3A:
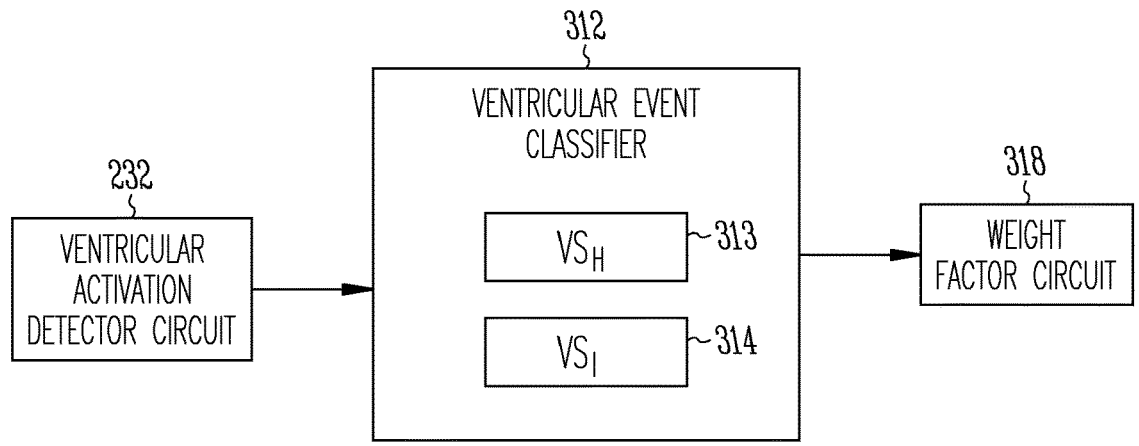
FIGS. 3A-3B are block diagrams illustrating portions of a system for determining weight factors and accordingly updating the HBP configuration.
Figure 3B:
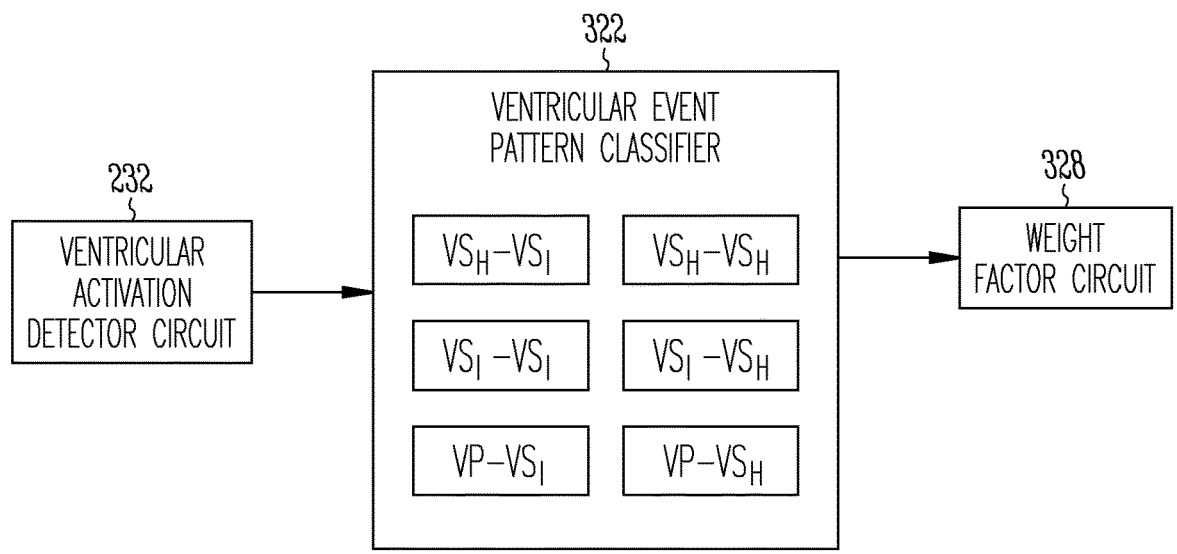

FIGS. 3A-3B are block diagrams illustrating portions of a system for determining weight factors and accordingly updating the HBP configuration such as the HPI. In particular, the system portion 310 as illustrated in FIG. 3A determines the weight factors using ventricular event type. The system portion 310, which is an embodiment of the control circuit 230, includes a ventricular activation detector circuit 232 configured to detect ventricular beats within a sensing window using physiologic signals sensed from a patient, and a ventricular event classifier circuit 312 configured to recognize the detected ventricular event as one of ventricular response to a captured HBP pulse $VS_H$ 313, or an intrinsically conducted ventricular activation $VS_I$ 314 due to atrial activations during AT. In an example, the classification between $VS_H$ 313 and $VS_I$ 314 may be based on timing information of the sensed ventricular activation with reference to a fiducial point. The ventricular event classifier circuit 312 may measure timing of ventricular activation using, e.g., a time delay with reference to a fiducial point, such as an atrial sensed (AS) event or an HBP pulse. The time delay may be compared to a threshold or range that is determined during normal sinus rhythm free of AT. The ventricular activation is classified as $VS_H$ 313 if the time interval falls below the threshold value, or as $VS_I$ 314 if the time interval exceeds the threshold value. In another example, $VS_H$ 313 and $VS_I$ 314 may be distinguished alternatively or additionally using signal morphology of the sensed ventricular activation. The ventricular event classifier circuit 312 may compare the morphology of the sensed ventricular activation to a morphology template of ventricular activation during normal sinus rhythm, and classify the ventricular activation as $VS_H$ 313 if a similarity metric to the morphology template falls below the threshold value, or as $VS_I$ 314 if the similarity metric to the morphology template exceeds the threshold value.

The system portion 310 includes a weight factor circuit 318, an embodiment of the weight factor circuit 233 in FIG. 2, that may determine weight factors for updating the HBP configuration, such as one or more of the weight factors "a" and "b" in Equation (1) above. In an example, the weight factor circuit 318 may determine the weight factor "b" based on the ventricular event type, including a first weight factor "$b_H$" for the measured ventricular cycle length (VCL) if the sensed ventricular activation is recognized as a $VS_H$, or a different second weight factor "$b_I$" for the measured VCL if the sensed ventricular activation is recognized as a $VS_I$. Additionally or alternatively, the weight factor circuit 318 may determine the weight factor "a" based on the ventricular event type, including a first factor "$a_H$" for the previous HPI (i.e., HPI (n−1)) if the sensed ventricular activation is a $VS_H$ event, or a different second factor "$a_I$" for the HPI(n−1) when the sensed ventricular activation is a $VS_I$ event. The recursive update of HPI, as shown in Equation (1) above, may be re-written as Equations (2) or (3) below, which correspond to respectively HPIs in the case of a $VS_H$ event or a $VS_I$ event:

$$HPI(n)=a_H*HPI(n-1)+b_H*VCL(n) \text{ (If beat } n \text{ is } VS_H) \quad (2)$$

$$HPI(n)=a_I*HPI(n-1)+b_I*VCL(n) \text{ (If beat } n \text{ is } VS_I) \quad (3)$$

In an example, the first weight factor "$b_H$" is greater than the second weight factor "$b_I$", such that VCL corresponding to a captured HBP and conducted ventricular response ($VS_H$) has more influence on the HPI than the VCL corresponding to an intrinsically conducted ventricular activation ($VS_I$) due to atrial activity. Similarly, the weight factor "$a_H$" may be greater than the weight factor "$a_I$", such that the previous HPI (i.e., HPI(n−1)) corresponding to a $VS_H$ beat has more influence on the next HPI (i.e., HPI (n)) than the previous HPI corresponding to a $VS_I$ beat. Because a $VS_H$ beat indicates HBP capture and conduction, while a $VS_I$ beat indicates intrinsic conduction due to atrial activity and likely non-capture by the HBP, the greater weights ($a_H$ and/or $b_H$) assigned for $VS_H$ beat than for $VS_I$ beat can promote effective use of HBP in regularizing ventricular rate during AT. Accordingly, according to Equations (2) and (3), the His-bundle paced $VS_H$ may lead to a larger HPI than the intrinsically conducted $VS_I$, hence a slower HBP pacing rate (HPR). The electrostimulation circuit 210 may stimulate the physiologic conduction pathway in accordance with the updated HBP configuration, such as the HPI as determined by Equations (2) or (3).

The system portion 320 as illustrated in FIG. 3B determines the weight factors using a ventricular event pattern. The ventricular event pattern refers to a context of the ventricular event type (e.g., a $VS_H$ or $VS_I$), which can be represented, in an example, by one or more previous ventricular activations followed by the recognized sensed ventricular activation. The previous ventricular activation may include one of a $VS_I$, a $VS_H$, or a ventricular paced event (VP). The system portion 320, which is an embodiment of the control circuit 230, includes a ventricular activation detector circuit 232 to detect ventricular beats within a sensing window using a physiologic signals sensed from a patient, and a ventricular event pattern classifier circuit 322 to detect a ventricular activation pattern. FIG. 3B illustrates some non-limiting examples of ventricular activation patterns represented by two consecutive ventricular beats of the same or distinct types: a $VS_H$ followed by a $VS_I$ ($VS_H$-$VS_I$ pattern), a $VS_I$ followed by a $VS_I$ ($VS_I$-$VS_I$ pattern), a VP followed by a $VS_I$ (VP-$VS_I$ pattern), a $VS_H$ followed by a $VS_H$ ($VS_H$-$VS_H$ pattern), a $VS_I$ followed by a $VS_H$ ($VS_I$-$VS_H$ pattern), or a VP followed by a $VS_H$ (VP-$VS_H$ pattern). The weight factor for the previous HBP pacing rate (i.e., "a" in Equation (1)) or the weight factor for the measured VCL (i.e., "b" in Equation (1)) may be respectively determined using information of the ventricular activation pattern.

In an example, if the present ventricular event is a $VS_I$ event, then the weight factors (one or both of "a" and "b") may be respectively set for activation patterns $VS_H$-$VS_I$, $VS_I$-$VS_I$, and VP-$VS_I$. In particular: (1) a $VS_H$-$VS_I$ pattern may indicate that the HPI was lengthened too far such that an intrinsic atrial impulse has escaped; accordingly, the weight factors can be set to shorten the HPI (i.e., HPI(n) <HPI(n−1)); (2) a $VS_I$-$VS_I$ pattern may indicate consecutive atrial impulses causing ventricular activation; accordingly, the weight factors can be set to shorten the HPI, thus more aggressive HBP may be delivered to increase the chance of HBP capture and conduction; (3) a VP-$VS_I$ pattern may indicate inadequate HBP capture; accordingly, the weight factors can be set to shorten the HPI to improve HBP capture and conduction.

In another example, if the present ventricular event is a $VS_H$ event, it indicates the current HBP setting (such as timing) is adequate for HBP capture and conduction. Consequently, the weight factors "a" and/or "b" can be set such that HPI is substantially maintained (i.e., HPI(n) is substantially equal to HPI(n−1)) regardless of previous ventricular activation event type (that is, for any of the activation patterns $VS_H$-$VS_H$, $VS_I$-$VS_H$, and VP-$VS_H$). Alternatively, small weight factors may be assigned for a $VS_I$-$VS_H$ pattern to shorten the HPI (i.e., HPI(n)<HPI(n−1)), and/or large weight factors may be assigned in the event of $VS_H$-$VS_H$ or VP-$VS_H$ patterns to lengthen the HPI (i.e., HPI(n)>HPI(n−1)). The electrostimulation circuit 210 may stimulate the physiologic conduction pathway in accordance with the updated HBP configuration, such as the HPI determined according to Equation (1).

Figure 4A:
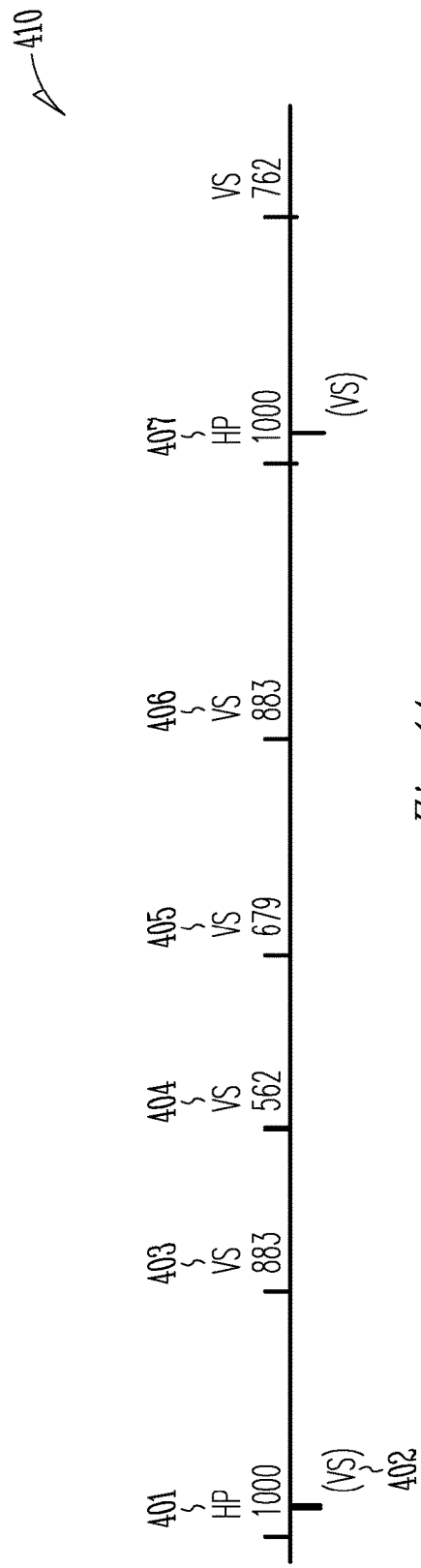
FIGS. 4A-4B are diagrams illustrating an example of ventricular rate regularization (VRR) using HBP according to a recursively determined and updated HBP configuration.
Figure 4B:
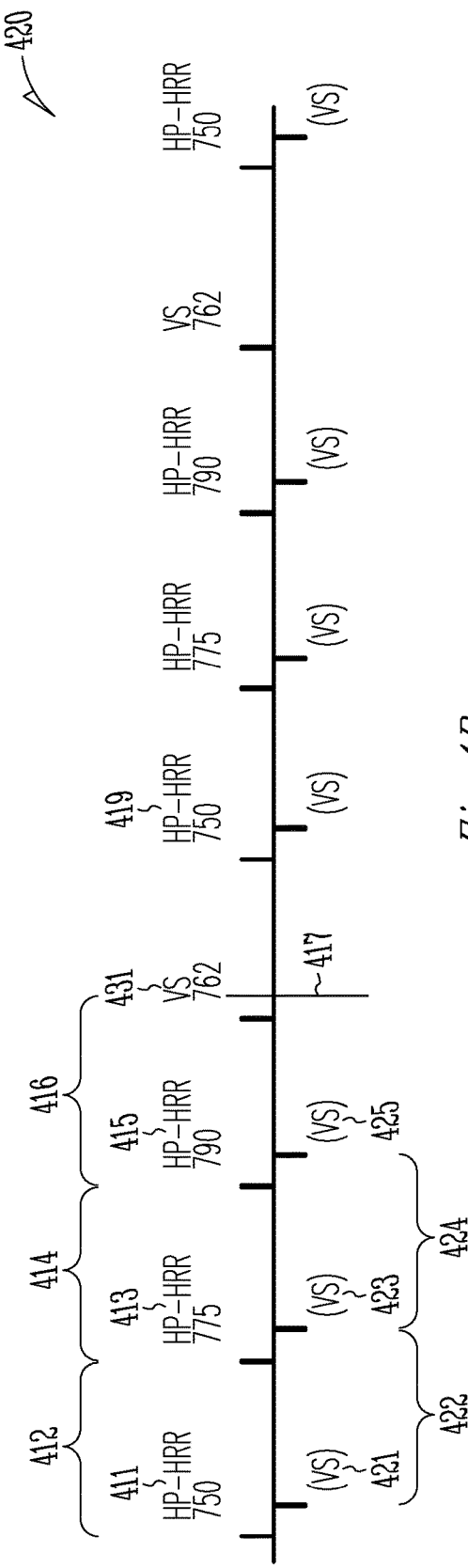

FIGS. 4A-4B are diagrams illustrating an example of ventricular rate regularization (VRR) using the HBP, such as delivered according to a recursively updated HBP configuration, as previously discussed. A medical device (e.g., the IMD 104) or the medical system 200 may controllably activate or deactivate the feature of HBP-based ventricular rate regularization (HRR) feature, such as according to Equation (1) or a variant thereof, such as Equation (2) or (3). FIGS. 4A and 4B each illustrate portions of marker channel diagrams 410 and 420 such as generated by the IMD 104 or the output unit of the user interface 240. A marker channel diagram depicts a sequence of detected cardiac events and their timings (in terms of delay in milliseconds from a reference time). Examples of the detected cardiac events, as illustrated in the marker channels 310 and 320, may include: an intrinsically conducted ventricular event "VS" due to atrial activation (also referred to as a $VS_I$ event as previously discussed); a ventricular event produced by HBP pulses "(VS)" that capture the His-bundle and conduct to the ventricles (also referred to as a $VS_H$ event as previously discussed); a His-bundle pacing event "HP" without the HRR feature (e.g., HRR feature being deactivated); and a His-bundle pacing event "HP-HRR" with the HRR feature (e.g., HRR feature being activated).

Diagram 410 in FIG. 4A illustrates cardiac events and their timings during an AT episode when the HRR feature is deactivated. In this example, the HBP is delivered in a demand mode at a specified HBP pacing rate of 60 bpm, such that an HBP pulse may be delivered if no intrinsic ventricular "VS" event is sensed within an HBP window of 1000 msec. However, if a "VS" event is sensed prior to the expiration of the HBP window, then the scheduled HBP is aborted. The diagram 410 illustrates that following an HP event 401 and a detection of resultant "(VS)" event 402, atrial impulses during an ongoing AT episode are intermittently conducted to the ventricle, resulting in a sequence of "VS" events 403-406 with substantially variable ventricular intervals. HBP pulses are sporadically delivered (e.g., no HP up until HP 407) during this period of AT episode because the atrial impulses conduct and activate the ventricles at a rate faster than 60 bpm (i.e., ventricular cycle lengths are shorter than 1000 msec). The fast and highly variable ventricular activation, represented by "VS" events 403-406 (e.g., 883 msec, 562 msec, 679 msec, 883 msec, 1000 msec, etc.), may cause various levels of symptoms in some patients, varying from heart palpitations, fainting, lightheadedness, shortness of breath, to chest pain. Chronic AT without correction of irregular ventricular rate may be associate with increased risk of heart failure, dementia, and stroke.

Diagram 420 in FIG. 4B illustrates cardiac events and their timings during an AT episode when the HRR feature is activated. The HBP pacing interval (HPI) may be determined dynamically on a beat-by-beat basis, such as according to Equation (1) or a variant thereof. In this example, HBP is delivered in a demand mode with a lower rate limit (LRL) of 80 bpm, such that an HBP pulse may be delivered if no intrinsic ventricular "VS" event is sensed within an HBP window of 750 msec. However, in response to an "(VS)" event (i.e., ventricular event due to HBP capture), the next HBP pulse may be delivered at HPI recursively determined, such as according to Equation (1). The diagram 420 illustrates that following an "HP-HRR" event 411 and a resultant "(VS)" event 421, timing for the next HP-HRR 413 is determined using Equation (1), and delivered at a 775 msec delay from the previous HP-HRR 411. Then, the HP-HRR pulse 413 elicits a ventricular activation (VS) 423. In response to the (VS) 423, timing of next HBP pulse HP-HRR 415, or the corresponding HPI 414 away from the HP-HRR pulse 413, may be determined using Equation (1), such as a weighted combination of a previous HBP interval 412 (between the HBP pacing pulses 411 and 413) immediately prior to the current HBP pulse 413, and the ventricular cycle length 422 between the previous (VS) 421 and the present (VS) 423. The next HBP pulse HP-HRR 415 may then be delivered upon the expiration of that timer (e.g., after 790 msec has passed from the pulse 414).

Similarly, upon detection of a ventricular event (VS) 425 due to the HBP pulse 415, timing for the next HBP pulse may be determined using Equation (1), which is an interval 416 following the HBP pulse 415. However, prior to the expiration of the duration 416, an intrinsic VS event 431 (produced by intermittent conducted atrial impulse during AT) is sensed; as a result, the next HP-HRR pulse that would have occurred at 417 is aborted. The electrostimulation circuit 210 may be configured to abort scheduled HBP pulse upon the expiration of the determined HBP pacing interval, and the pacing configuration circuit 236 may reset the HBP pacing interval with reference to the sensed intrinsic ventricular event VS. As illustrated in FIG. 4B, the intrinsic VS event 431 may reset the timing of next HBP pulse HP-HRR 419 to be a delivered at the specified LRL, which is 750 msec from the VS event 431. The example in FIG. 4B thus illustrated the HRR feature, when activated, may substantially reduce the variability in ventricular cycle lengths (e.g., 750 msec, 775 msec, 790 msec, 762 msec, etc.), thus achieving rate control and improved ventricular function during AT.

Figure 5:
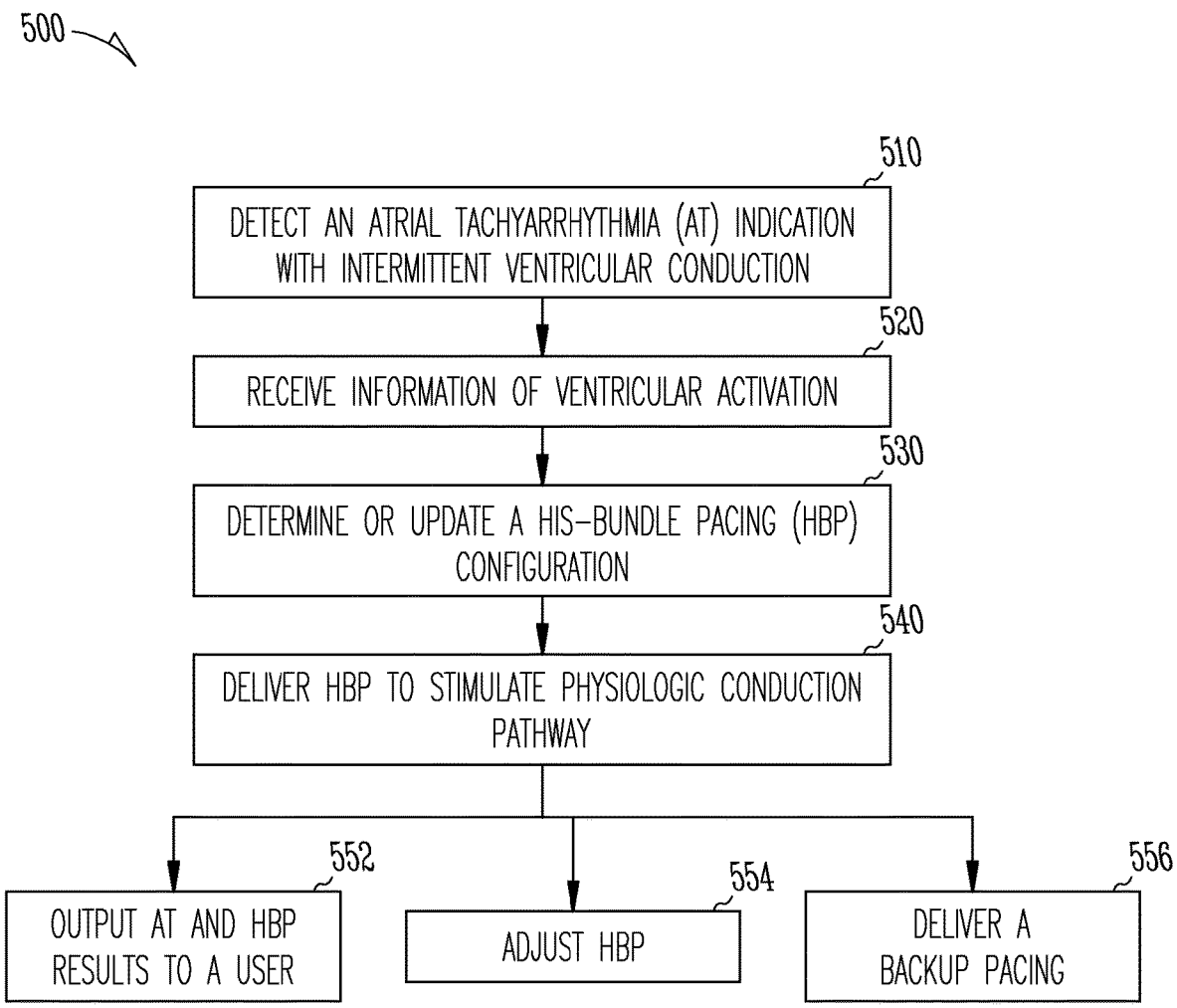
FIG. 5 is a flowchart illustrating generally an example of a method for providing HBP to a patient using a medical system.

FIG. 5 is a flowchart illustrating generally an example of a method 500 for providing His-bundle pacing (HBP) to a patient using a medical system. In particular, the method 500 may be used to stimulate a His bundle or other parts of a physiologic conduction pathway to regularize ventricular rate, and achieve ventricular rate control during atrial tachyarrhythmia (e.g., AF or AFL). The method 500 may be implemented and executed in an ambulatory medical device such as an implantable or wearable medical device, or in a remote patient management system. In an example, the method 500 may be implemented in, and executed by, the IMD 104, one or more devices in the external system 140, or the His-bundle pacing system 200.

The method 500 commences at 510, where an indication of atrial tachyarrhythmia (AT) with intermittent ventricular conduction may be detected, such as using the AT detector circuit 222. Examples of the AT episodes with intermittent ventricular conduction include AF or AFL episodes with irregular ventricular contractions. Information of cardiac activities at one or more cardiac chambers or cardiac sites, such as sensed by the sensing circuit 220, may be used to detect said AT events. By way of example and not limitation, an AT indication may be detected using fast atrial activation (e.g., atrial rate exceeding a threshold), fast and/or irregular ventricular contractions (e.g., variability of ventricular rate sensed from ventricular electrical or mechanical signals or FFVA signals), fast and/or irregular evoked responses sensed at the His-bundle or a bundle branch produced by atrial contractions during AT. The AT indication may also be detected using a change in pacing statistics, such as a decrease in HBP pulse delivery (e.g., HBP delivery frequency falls below an HBP frequency threshold). In some examples for patients having a pacing system (e.g., a pacemaker) programmed to switch between an atrial tracking mode and a non-tracking mode as part of an atrial tachy response (ATR), the AT indication may be detected when the pacing mode transits from the atrial tracking-mode to the non-atrial tracking mode. The detected AT episode likely terminates when the pacing mode falls back to the tracking mode.

At 520, information of ventricular activation may be received, such as from physiologic signals (e.g., ventricular EGM, FFVA signals, or cardiac mechanical signals) collected by the sensing circuit 220, or from a data storage device that store the ventricular activation information collected from the patient. The ventricular activation information may include information about ventricular beats, and ventricular cycle length and/or ventricular heart rate. The ventricular cycle length or ventricular heart rate may be used to determine or adjust an HBP pacing configuration.

At 530, an HBP configuration may be determined or adjusted in response to the detection of AT indication indicating presence of an AT episode with irregular ventricular rates. The process of determining the HBP configuration may be implemented and executed by the pacing configuration circuit 236. In an example, the pacing configuration circuit 236 may adjust the HBP configuration on a beat-by-beat basis using the detected ventricular beats. Examples of the HBP configuration may include HBP pacing interval (HPI, the time interval between adjacent HBP pulses), pacing rate, or timing of HBP pulse relative to a reference point, among other pacing parameters. One or more of these HBP parameters may be determined or adjusted, such that the HBP may regularize His bundle activations and, with effective HBP capture and conduction through the physiologic pathway, regularize ventricular rate during AT, and improve cardiac performance with ventricular rate control during AT. In an example, the HPI may be updated recursively using a weighted combination of a previously determined HPI and a ventricular cycle length (VCL) corresponding to the presently detected beat, such as discussed above with reference to Equation (1). The weight factors that control the respective impacts of the historical HPI and the sensed VCL may be user programmable. Alternatively, these weight factors may be automatically determined or adjusted. In an example, one or more of said weight factors may be determined using ventricular event type. In another example, the weight factor may be determined or adjusted using information about a ventricular event pattern, such as a sequence of sensed ventricular events of the same or different types. Examples of a method of determining or adjusting the HBP configuration using ventricular event type, or ventricular event pattern are discussed below, such as with reference to FIG. 6.

At 540, HBP pulses may be generated and delivered to a target site to stimulate patient physiologic conduction pathway, such as by the electrostimulation circuit 210. The target site may include an interventricular septum region or a right atrial region near the His-bundle, or other conductive tissue such as right or left bundle branches or fascicles, or Purkinje fibers. Delivery of the HBP pulses may be carried out using a lead with electrodes associated therewith, such as one or more of the electrodes 112A-112B on the lead 106. The HBP pulses may be generated and delivered in accordance with the HBP configuration determined or adjusted at 530.

The HBP pulses may be delivered at a particular time delay relative to a ventricular sensed event (VS) or an atrial sensed event (AS), or at a particular rate or HPI, such that the resultant HBP pulse, when capturing the His-bundle and conducting to the ventricles, may elicit ventricular contractions at controlled timings, thereby regularizing ventricular rates during AT. In some examples, in addition to the HBP configuration as determined or updated at 530, the delivery of HBP at 540 may further be in accordance with one or more other parameters such as stimulation site, stimulation strength, or stimulation mode. For example, the HBP may be delivered in a His-bundle only mode, an atrial-Hisian (AH) pacing mode, a His-ventricular (HV) pacing mode, or an atrial-His-ventricular (AHV) pacing mode. Additionally or alternatively, HBP capture verification and/or HBP threshold test may be performed at 540 to determine an appropriate HBP stimulation strength that, when HBP pulses are delivered in accordance with the HBP configuration as determined at 530, may capture the His bundle (e.g., selective or non-selective His-bundle capture) and thus effectuate ventricular rate regularization during AT.

In addition to HBP for ventricular rate regularization during AT, at 540, cardiac pacing of other modalities may be delivered to restore or improve cardiac synchrony and improve overall cardiac performance, including, for example, unipolar or bipolar bradycardia pacing, cardiac resynchronization therapy (CRT), BiV pacing, synchronized left ventricle (LV)-only pacing, single site pacing of only one site of a heart chamber (e.g., the left ventricle), or multisite pacing (MSP) of two or more sites of a heart chamber within the same cardiac cycle (e.g., multisite LV pacing). In an example, the HBP threshold may be determined based on a QRS width or QRS morphology that may be extracted from a ventricular EGM or a FFVA signal.

At 552, diagnostic and therapeutic information such as the detected AT episodes, atrial or ventricular rates, rate stability, and HBP configuration as determined at 530, may be output to a user (e.g., a clinician or the patient), such as being displayed on a display of the user interface 240. The ventricular event types and/or ventricular event pattern, and marker channels with event identifiers and information about relative timing, among other intermediate measurements or computations, may also be displayed.

Additionally or alternatively, at 554, one or more HBP parameters may be adjusted, such as based on patient response to the HBP delivered at 540. For example, the variability of ventricular rates may be reevaluated during and following the HBP delivery. If ventricular rate regularization is not satisfactory (e.g., variability of ventricular rates exceed a threshold), this may suggest that HBP is not capturing (e.g., para-Hisian capture or LOC), then the HBP therapy may be adjusted. The adjustment may include switching to a different HBP pacing site, or using pacing vector configuration. In an example, the HBP pacing vector may be reconfigured to deliver HBP pulses from a second His bundle site more distal than the first His bundle site, or to deliver HBP pulses from a left bundle branch site. In another example, the adjustment may include adjusting HBP pulse timing, stimulation strength such as one or more of pulse amplitude, pulse width, pulse frequency, pulse waveform, duty cycle, or stimulation duration. In some examples, the HBP adjustment may be based on capture statistics computed using the capture verification results over multiple heart beats. Examples of the capture statistics may include percentages, histograms, or other measures of distribution of the selective His-bundle capture, non-selective His-bundle capture, or para-Hisian capture.

At 556, a backup pacing may be delivered when certain capture status results, such as a LOC, or a para-Hisian capture. The backup pacing may be delivered to a target ventricular site via a lead with associated electrodes disposed in or on a ventricle, such as a right ventricle. Additionally or alternatively, the backup pacing may be delivered at or near the His bundle. In an example, the backup pacing pulses include high-output pacing (HOP) pulses with higher pacing energy than conventional pacing pulses. In some examples, the HOP pulses may be delivered on an intermittent basis, such that the conventional pacing pulses are delivered in 3-5 cardiac cycles between the HOP pulses. In addition to backup ventricular pacing, other therapies, such as CRT, BiV pacing, LV-only pacing, single site LV pacing, or multi-site LV pacing may be delivered to improve myocardial contractility and cardiac performance.

Figure 6:
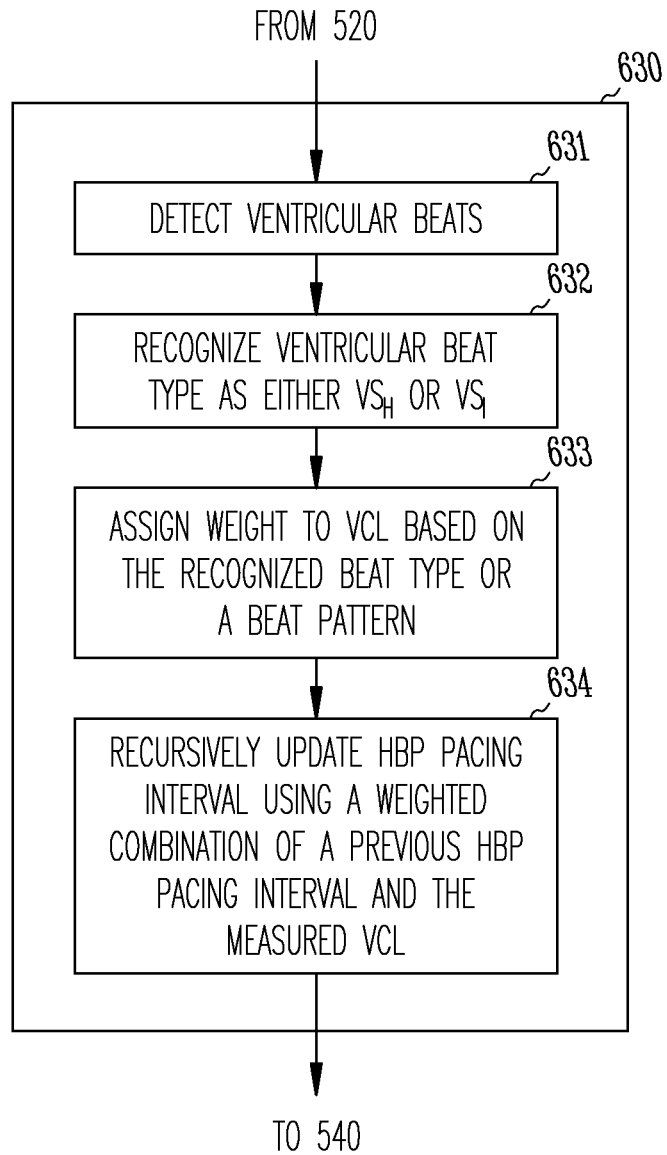

FIG. 6 is a block diagram illustrating an example of a method 630 for adjusting an HBP configuration during AT to regularize ventricular rate during AT. The adjustment of HBP configuration involves using ventricular beat type or beat pattern. The method 630 is an embodiment of a portion of the method 500, such as step 530 for determining or updating the HBP configuration. The method 630 may be implemented in and executed by the control circuit 230 as shown in FIG. 2, or a variation thereof, such as the system portions 310 or 320.

The method 630 begins at 631, where ventricular beats may be detected, such as from a physiologic signal (e.g., ventricular electrical or mechanical signals or FFVA signals). AT 632, the detected ventricular beats may be recognized as either a $VS_H$ beat, or a $VS_I$ beat, such as using the ventricular event classifier circuit 312. A $VS_H$ beat is a ventricular sensed event due to HBP pulses that capture the His-bundle and conduct to the ventricles. A $VS_I$ beat is an intrinsically conducted ventricular activation due to atrial activations during AT. Classification between $VS_H$ and $VS_I$ may be based on timing information or morphology of the sensed ventricular activation.

At 633, distinct weights, corresponding to $VS_H$ or $VS_I$ events, may be assigned to a ventricular cycle length (VCL). The weighted VCL may be used to update the HBP configuration, such as the HPI, according to Equation (1). In an example, the weight factor corresponding to a $VS_H$ event may be higher than weight factor corresponding to a $VS_I$ event. As such, the VCL corresponding to a $VS_H$ event has more influence on the HPI than the VCL corresponding to a $VS_I$ event. Additionally or alternatively, distinct weight factor for the previous HPI (i.e., HPI (n−1) in Equation (1)) may also be determined for a $VS_H$ event or a $VS_I$ event, such as illustrated in Equations (2) and (3) discussed above. Because a $VS_H$ beat indicates HBP capture and conduction, while a $VS_I$ beat indicates intrinsic conduction due to atrial activity and likely non-capture by the HBP, the greater weights ($a_H$ and/or $b_H$) assigned for $VS_H$ beat than for $VS_I$ beat can promote effective use of HBP in regularizing ventricular rate during AT.

In some examples, distinct weight factors may be assigned to the VCL or the previous HPI (i.e., HPI (n−1) in Equation (1)) based on a ventricular event pattern. The ventricular event pattern is a context of the presently detected ventricular event type, and may be represented by one or more previous ventricular activations (e.g., one of a $VS_I$, a $VS_H$, or a ventricular paced event VP), followed by the recognized sensed ventricular activation (e.g., $VS_H$ or $VS_I$). Examples of the ventricular activation patterns may include: a $VS_H$ followed by a $VS_I$ ($VS_H$-$VS_I$ pattern), a $VS_I$ followed by a $VS_I$($VS_I$-$VS_I$ pattern), a VP followed by a $VS_I$ (VP-$VS_I$ pattern), a $VS_H$ followed by a $VS_H$ ($VS_H$-$VS_H$ pattern), a $VS_I$ followed by a $VS_H$ ($VS_I$-$VS_H$ pattern), or a VP followed by a $VS_H$ (VP-$VS_H$ pattern). One or more of the weight factors may be determined based on the determined ventricular activation pattern, such as described above with reference to FIG. 3B.

At 634, HBP configuration, such as an HBP pacing interval (HPI), may be recursively updated using a weighted combination of a previous HBP pacing interval and the measured VCL, such as using one of the Equations (1)-(3) with the weights factors determined at step 633. The HPI thus determined may be dependent on the ventricular event type or event pattern. HBP pulses may then be delivered in accordance with the determined HPI to stabilize His-bundle pacing and hence regularize ventricular rate.

Figure 7:
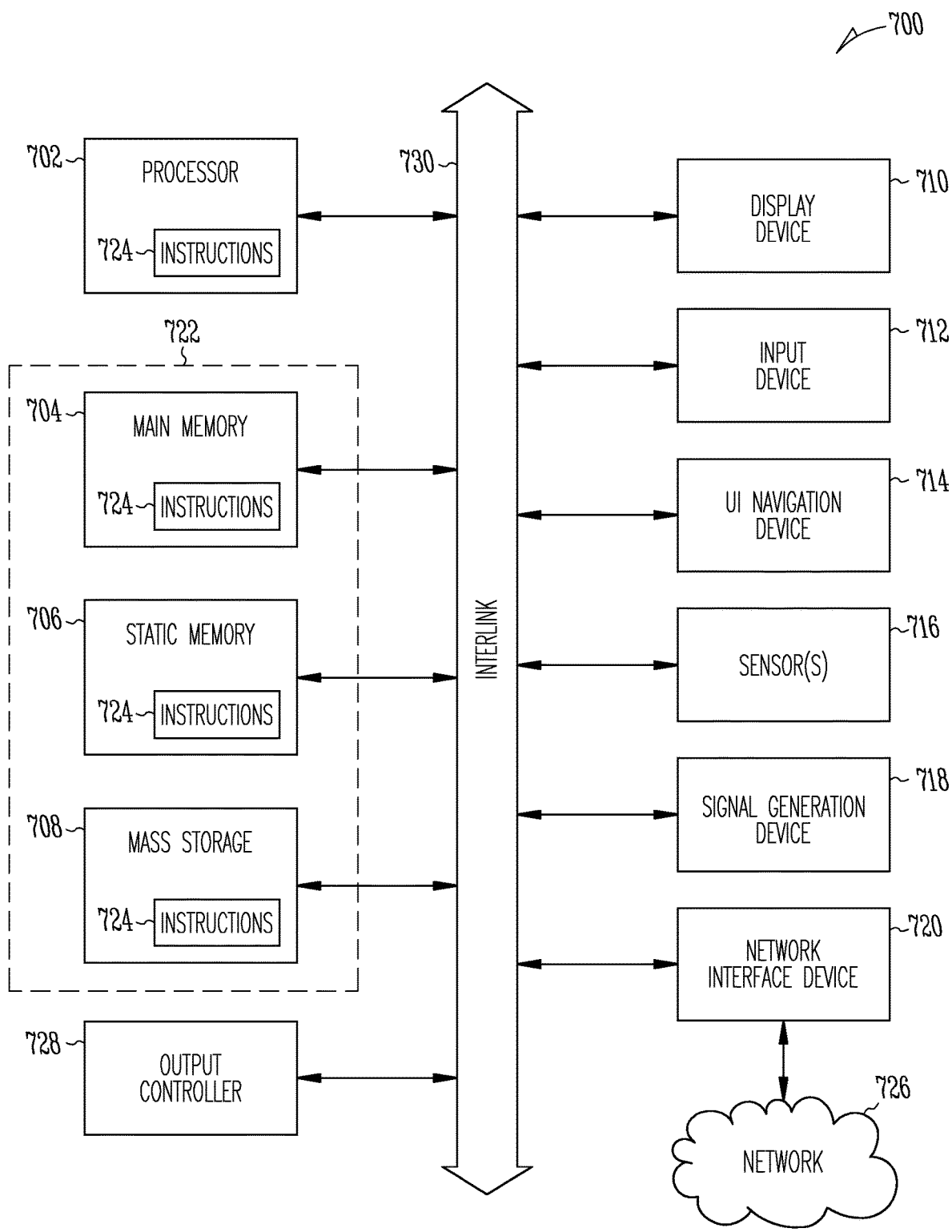
FIG. 7 illustrates a block diagram of an example machine upon which any one or more of the techniques (e.g., methodologies) discussed herein may perform.

FIG. 7 illustrates a block diagram of an example machine 700 upon which any one or more of the techniques (e.g., methodologies) discussed herein may perform. Portions of this description may apply to the computing framework of one or more of the medical devices described herein, such as the IMD, the external programmer, etc.

Examples, as described herein, may include, or may operate by, logic or a number of components, or mechanisms in the machine 700. Circuitry (e.g., processing circuitry) is a collection of circuits implemented in tangible entities of the machine 700 that include hardware (e.g., simple circuits, gates, logic, etc.). Circuitry membership may be flexible over time. Circuitries include members that may, alone or in combination, perform specified operations when operating. In an example, hardware of the circuitry may be immutably designed to carry out a specific operation (e.g., hardwired). In an example, the hardware of the circuitry may include variably connected physical components (e.g., execution units, transistors, simple circuits, etc.) including a machine-readable medium physically modified (e.g., magnetically, electrically, moveable placement of invariant massed particles, etc.) to encode instructions of the specific operation. In connecting the physical components, the underlying electrical properties of a hardware constituent are changed, for example, from an insulator to a conductor or vice versa. The instructions enable embedded hardware (e.g., the execution units or a loading mechanism) to create members of the circuitry in hardware via the variable connections to carry out portions of the specific operation when in operation. Accordingly, in an example, the machine-readable medium elements are part of the circuitry or are communicatively coupled to the other components of the circuitry when the device is operating. In an example, any of the physical components may be used in more than one member of more than one circuitry. For example, under operation, execution units may be used in a first circuit of a first circuitry at one point in time and reused by a second circuit in the first circuitry, or by a third circuit in a second circuitry at a different time. Additional examples of these components with respect to the machine 700 follow.

In alternative embodiments, the machine 700 may operate as a standalone device or may be connected (e.g., networked) to other machines. In a networked deployment, the machine 700 may operate in the capacity of a server machine, a client machine, or both in server-client network environments. In an example, the machine 700 may act as a peer machine in peer-to-peer (P2P) (or other distributed) network environment. The machine 700 may be a personal computer (PC), a tablet PC, a set-top box (STB), a personal digital assistant (PDA), a mobile telephone, a web appliance, a network router, switch or bridge, or any machine capable of executing instructions (sequential or otherwise) that specify actions to be taken by that machine. Further, while only a single machine is illustrated, the term "machine" shall also be taken to include any collection of machines that individually or jointly execute a set (or multiple sets) of instructions to perform any one or more of the methodologies discussed herein, such as cloud computing, software as a service (SaaS), other computer cluster configurations.

The machine (e.g., computer system) 700 may include a hardware processor 702 (e.g., a central processing unit (CPU), a graphics processing unit (GPU), a hardware processor core, or any combination thereof), a main memory 704, a static memory (e.g., memory or storage for firmware, microcode, a basic-input-output (BIOS), unified extensible firmware interface (UEFI), etc.) 706, and mass storage 708 (e.g., hard drive, tape drive, flash storage, or other block devices) some or all of which may communicate with each other via an interlink (e.g., bus) 730. The machine 700 may further include a display unit 710, an alphanumeric input device 712 (e.g., a keyboard), and a user interface (UI) navigation device 714 (e.g., a mouse). In an example, the display unit 710, input device 712, and UI navigation device 714 may be a touch screen display. The machine 700 may additionally include a signal generation device 718 (e.g., a speaker), a network interface device 720, and one or more sensors 716, such as a global positioning system (GPS) sensor, compass, accelerometer, or one or more other sensors. The machine 700 may include an output controller 728, such as a serial (e.g., universal serial bus (USB), parallel, or other wired or wireless (e.g., infrared (IR), near field communication (NFC), etc.) connection to communicate or control one or more peripheral devices (e.g., a printer, card reader, etc.).

Registers of the processor 702, the main memory 704, the static memory 706, or the mass storage 708 may be, or include, a machine-readable medium 722 on which is stored one or more sets of data structures or instructions 724 (e.g., software) embodying or utilized by any one or more of the techniques or functions described herein. The instructions 724 may also reside, completely or at least partially, within any of registers of the processor 702, the main memory 704, the static memory 706, or the mass storage 708 during execution thereof by the machine 700. In an example, one or any combination of the hardware processor 702, the main memory 704, the static memory 706, or the mass storage 708 may constitute the machine-readable medium 722. While the machine-readable medium 722 is illustrated as a single medium, the term "machine-readable medium" may include a single medium or multiple media (e.g., a centralized or distributed database, and/or associated caches and servers) configured to store the one or more instructions 724.

The term "machine-readable medium" may include any medium that is capable of storing, encoding, or carrying instructions for execution by the machine 700 and that cause the machine 700 to perform any one or more of the techniques of the present disclosure, or that is capable of storing, encoding or carrying data structures used by or associated with such instructions. Non-limiting machine-readable medium examples may include solid-state memories, optical media, magnetic media, and signals (e.g., radio frequency signals, other photon based signals, sound signals, etc.). In an example, a non-transitory machine-readable medium comprises a machine-readable medium with a plurality of particles having invariant (e.g., rest) mass, and thus are compositions of matter. Accordingly, non-transitory machine-readable media are machine-readable media that do not include transitory propagating signals. Specific examples of non-transitory machine-readable media may include: non-volatile memory, such as semiconductor memory devices (e.g., Electrically Programmable Read-Only Memory (EPROM), Electrically Erasable Programmable Read-Only Memory (EEPROM)) and flash memory devices; magnetic disks, such as internal hard disks and removable disks; magneto-optical disks; and CD-ROM and DVD-ROM disks.

The instructions 724 may be further transmitted or received over a communications network 726 using a transmission medium via the network interface device 720 utilizing any one of a number of transfer protocols (e.g., frame relay, internet protocol (IP), transmission control protocol (TCP), user datagram protocol (UDP), hypertext transfer protocol (HTTP), etc.). Example communication networks may include a local area network (LAN), a wide area network (WAN), a packet data network (e.g., the Internet), mobile telephone networks (e.g., cellular networks), Plain Old Telephone (POTS) networks, and wireless data networks (e.g., Institute of Electrical and Electronics Engineers (IEEE) 802.11 family of standards known as Wi-Fi®, IEEE 802.16 family of standards known as WiMax®), IEEE 802.15.4 family of standards, peer-to-peer (P2P) networks, among others. In an example, the network interface device 720 may include one or more physical jacks (e.g., Ethernet, coaxial, or phone jacks) or one or more antennas to connect to the communications network 726. In an example, the network interface device 720 may include a plurality of antennas to wirelessly communicate using at least one of single-input multiple-output (SIMO), multiple-input multiple-output (MIMO), or multiple-input single-output (MISO) techniques. The term "transmission medium" shall be taken to include any intangible medium that is capable of storing, encoding or carrying instructions for execution by the machine 700, and includes digital or analog communications signals or other intangible medium to facilitate communication of such software. A transmission medium is a machine-readable medium.

Various embodiments are illustrated in the figures above. One or more features from one or more of these embodiments may be combined to form other embodiments. Method examples described herein may be machine or computer-implemented at least in part. Some examples may include a computer-readable medium or machine-readable medium encoded with instructions operable to configure an electronic device or system to perform methods as described in the above examples. An implementation of such methods may include code, such as microcode, assembly language code, a higher-level language code, or the like. Such code may include computer readable instructions for performing various methods. The code may form portions of computer program products. Further, the code may be tangibly stored on one or more volatile or non-volatile computer-readable media during execution or at other times.

The above detailed description is intended to be illustrative, and not restrictive. The scope of the disclosure should, therefore, be determined with references to the appended claims, along with the full scope of equivalents to which such claims are entitled.

What is claimed is:

1. A medical-device system, comprising:
    an arrhythmia detector circuit configured to detect an atrial tachyarrhythmia (AT) indication with intermittent ventricular conduction in a patient; and
    a control circuit configured to:
        receive information of ventricular activation;
        in response to a detected AT indication, determine a His-bundle pacing (HBP) configuration using the received information of ventricular activation; and
        control an electrostimulation circuit configured to generate HBP pulses, and provide a control signal to deliver the generated HBP pulses to stimulate a physiologic conduction pathway of a heart of the patient in accordance with the determined HBP configuration to regularize ventricular activation rate.

2. The system of claim 1, including the electrostimulation circuit, wherein:
    the control circuit is configured to detect ventricular beats from the received information of ventricular activation, and in response to the detected AT indication, update the HBP configuration on a beat-by-beat basis using the detected ventricular beats; and
    the electrostimulation circuit is configured to stimulate the physiologic conduction pathway in accordance with the updated HBP configuration.

3. The system of claim 2, wherein the HBP configuration includes an HBP pacing interval, and the control circuit is configured to measure a ventricular cycle length (VCL) of the detected ventricular beats, and to update the HBP pacing interval using a weighted combination of a previous HBP pacing interval and the measured VCL each scaled by respective weight factors.

4. The system of claim 3, wherein, in response to an intrinsic ventricular activation sensed prior to expiration of the determined HBP pacing interval:
    the electrostimulation circuit is configured to abort stimulation of the physiologic conduction pathway upon the expiration of the determined HBP pacing interval; and
    the control circuit is configured to reset the HBP pacing interval with reference to the sensed intrinsic ventricular activation.

5. The system of claim 3, wherein the control circuit is configured to determine the HBP pacing interval to be within a specified range between a lower pacing rate limit and a maximum pacing rate limit.

6. The system of claim 3, wherein the control circuit is configured to:
    recognize the sensed ventricular activation as either a ventricular response to the HBP pulses ($VS_H$) or an intrinsically conducted ventricular activation ($VS_I$); and
    determine one or more of the respective weight factors for the previous HBP pacing rate and for the measured VCL using the recognized sensed ventricular activation.

7. The system of claim 6, wherein the control circuit is configured to determine a first weight factor for the measured VCL if the sensed ventricular activation is recognized as a $VS_H$, and to determine a second weight factor, smaller than the first weight factor, for the measured VCL if the sensed ventricular activation is recognized as a $VS_I$.

8. The system of claim 6, wherein the control circuit is configured to increase the HBP pacing interval if the sensed ventricular activation is recognized as a $VS_H$, or to decrease the HBP pacing interval if the sensed ventricular activation is recognized as a $VS_I$.

9. The system of claim 6, wherein the control circuit is configured to recognize the sensed ventricular activation as either a $VS_H$ or a $VS_I$ using timing or morphology information of the sensed ventricular activation with reference to a fiducial point.

10. The system of claim 6, wherein the control circuit is further configured to:
    determine a ventricular activation pattern including one or more previous ventricular activations followed by the recognized sensed ventricular activation, the one or more previous ventricular activations each including a $VS_I$, a $VS_H$, or a ventricular paced (VP) event; and
    determine one or more of the respective weight factors for the previous HBP pacing rate and for the measured VCL using the determined ventricular activation pattern.

11. The system of claim 10, wherein the ventricular activation pattern includes one of:
    a $VS_H$ followed by a $VS_I$;
    a $VS_I$ followed by a $VS_I$;
    a VP followed by a $VS_I$;
    a $VS_H$ followed by a $VS_H$;
    a $VS_I$ followed by a $VS_H$; or
    a VP followed by a $VS_H$.

12. The system of claim 3, wherein the control circuit is configured to:
    detect a fusion between an intrinsically His bundle activation and an HBP pulse using timing information or morphology of the sensed ventricular activation; and recognize the sensed ventricular activation as a $VS_I$ in response to the detected fusion.

13. The system of claim 1, wherein the control circuit is configured to determine the HBP configuration including an HBP pacing rate, an HBP pacing interval, or HBP pacing timing.

14. A method for pacing a physiologic conduction pathway including a His bundle or a bundle branch of the heart, the method comprising:
  detecting an atrial tachyarrhythmia (AT) indication with intermittent ventricular conduction;
  receiving information of ventricular activation;
  in response to the detected AT indication, determining a His-bundle pacing (HBP) configuration using the received information of ventricular activation; and
  delivering HBP pulses to stimulate the physiologic conduction pathway in accordance with the determined HBP configuration to regularize ventricular activation rate.

15. The method of claim 14, wherein determining the HBP configuration includes:
  detecting ventricular beats from the received information of ventricular activation; and
  updating the HBP configuration on a beat-by-beat basis using the detected ventricular beats.

16. The method of claim 15, wherein determining the HBP configuration includes:
  measuring a ventricular cycle length (VCL) corresponding to the detected ventricular beats; and
  updating an HBP pacing interval using a weighted combination of a previous HBP pacing interval and the measured VCL each scaled by respective weight factors.

17. The method of claim 16, comprising:
  recognizing the sensed ventricular activation as either a ventricular response to the HBP pulses ($VS_H$) or an intrinsically conducted ventricular activation ($VS_I$); and
  determining one or more of the respective weight factors for the previous HBP pacing rate and for the measured VCL using the recognized sensed ventricular activation.

18. The method of claim 17, wherein determining the one or more of the respective weight factors including:
  determining a first weight factor for the measured VCL if the sensed ventricular activation is recognized as a $VS_H$; and
  determining a second weight factor, smaller than the first weight factor, for the measured VCL if the sensed ventricular activation is recognized as a $VS_I$.

19. The method of claim 17, comprising:
  increasing the HBP pacing interval if the sensed ventricular activation is recognized as a $VS_H$; and
  decreasing the HBP pacing interval if the sensed ventricular activation is recognized as a $VS_I$.

20. The method of claim 17, comprising:
  determining a ventricular activation pattern including one or more previous ventricular activations followed by the recognized sensed ventricular activation, the one or more previous ventricular activations each including a $VS_I$, a $VS_H$, or a ventricular paced (VP) event; and
  determining one or more of the respective weight factors for the previous HBP pacing rate and for the measured VCL using the determined ventricular activation pattern.

* * * * *